(12) United States Patent
Barron et al.

(10) Patent No.: US 7,531,073 B2
(45) Date of Patent: May 12, 2009

(54) SPARSELY CROSS-LINKED NANOGELS: A NOVEL POLYMER STRUCTURE FOR MICROCHANNEL DNA SEQUENCING

(75) Inventors: Annelise Barron, Evanston, IL (US); Erin Doherty, Wilmington, DE (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 12/137,291

(22) Filed: Jun. 11, 2008

(65) Prior Publication Data

US 2009/0011420 A1    Jan. 8, 2009

Related U.S. Application Data

(62) Division of application No. 11/037,561, filed on Jan. 18, 2005, now Pat. No. 7,399,396.

(60) Provisional application No. 60/536,879, filed on Jan. 16, 2004.

(51) Int. Cl.
*G01N 27/26*    (2006.01)
(52) U.S. Cl. .................. 204/470; 204/469; 204/606
(58) Field of Classification Search ............. 204/470, 204/469, 606
See application file for complete search history.

(56) References Cited

U.S. PATENT DOCUMENTS

| | | | |
|---|---|---|---|
| 5,213,669 | A | 5/1993 | Guttman |
| 5,296,116 | A | 3/1994 | Guttmann |
| 5,332,481 | A | 7/1994 | Guttmann |
| 5,370,777 | A | 12/1994 | Guttmann et al. |
| 5,421,980 | A | 6/1995 | Guttmann |
| 5,873,991 | A * | 2/1999 | Gothe et al. ............ 204/470 |
| 6,333,051 | B1 | 12/2001 | Kabanov et al. |
| 6,696,089 | B2 | 2/2004 | Kabanov et al. |

OTHER PUBLICATIONS

Fung, E. N., et al. Anal. Chem. 1995, 67 (13), 1913-1919.
Gao, Q. F., et al. Anal. Chem. 1998, 70 (7), 1382-1388.
Salas-Solano, O., et al. Anal. Chem. 1998, 70 (19), 3996-4003.
Albarghouthi, M. N., et al. Electrophoresis 2001, 22, 737-747.
Albarghouthi, M. N., et al. Electrophoresis 2002, 23 (10), 1429-1440.
Buchholz, B. A., et al. Anal. Chem. 2001, 73, 157-164.
Heller, C., et al. Electrophoresis 1999, 20, 1962-1977.
Carrilho, E., et al. Anal. Chem. 1996, 68 (19), 3305-3313.
Zhou, H., et al. Anal. Chem. 2000, 72 (5), 1045-1052.
Ugaz, V. M., et al. Electrophoresis 2002, 23 (16), 2777-2787.
Hunkeler, D. J., Macromolecules 1991, 24 (9), 2160.
Sakai, T., Yoshida, R. Langmuir 2004, 20, 1036.
Jones, C., Lyon, A. Macromolecules 2003, 36, 1988.
Lu, X., Hu, Z., Gao, J. Macromolecules 2000, 33, 8698.
Zhou, S., Chu, B. J. Phys. Chem. B 1998, 102, 1364.
Ogawa, K.; Nakayama, A.; Kokufuta, E. Langmuir 2003, 19, 3178.
Kazakov, S.; Kaholek, M.; Teraoka, I.; Levon, K. Macromolecules 2002, 35, 1911.
Oh, K.; Oh, J.; Choi, H.; Bae, Y. Macromolecules 1998, 31, 7328.
Berndt, I.; Richtering, W. Macromolecules 2003, 36, 8780.
Ito et al., E. Langmuir 1999, 15, 4289.
Idziak, I.; Avoce, D.; Lessard, D.; Gravel, D.; Zhu, X. Macromolecules 1999, 32, 1260.
Siu, M.; Liu, H.; Zhu, X.; Wu, C. Macromolecules 2003, 36, 2103.
Liang, D., et al., 1999 Macromolecules 32: 6326—63332.
Sudor, J., et al., 2001 Electrophoresis 22: 720-728.
Liu, T., et al., 2001 Electrophoresis 22: 449-458.
Arshady, R., Colloid Polym. Sci. 1992, 270 (8), 717-732.
Hunkeler, D., Polym. Int. 1992, 27 (1), 23-33.
Baade, W., Reichert, K. H., Eur. Polym. J. 1984, 20, 505-512.
Pelton, R. Adv. Colloid Interface Sci. 2000, 85, 1.
McAllister, K.; et al., J. JACS 2002, 124, 15198.
Heiger, D. N., et al. Chromatogr. 1990, 33-48.
Guttman, A., et al. Anal. Chem. 1990, 62 (2), 137-141.
Harke, H. R., et al. J. Chromatogr. 1992, 608, 143-150.
Smith, L. M. Nature 1991, 349 (6312), 812-813.
Drossman, H., et al. Analytical Chemistry 1990, 62 (9), 900-903.
Luckey, J. A., et al. Nucleic Acids Research 1990, 18 (15), 4417-4421.
Baba, Y., et al. Anal. Chem. 1992, 64 (11), 1221-1225.
Bae, Y.C., et al. J. Chromatogr. A 1993, 652, 17-22.
Ruiz-Martinez, M. C., et al. Anal. Chem. 1993, 65, 2851-2858.
Cohen, A. S., et al. Journal of Chromatography 1990, 516 (1), 49.
Slater, G. W., Noolandi, J. Biopolymers 1986, 25, 431-454.
Goetzinger W., et al., Electrophoresis 1998 1, 242-248.
Barron, A. E., et al. Electrophoresis 1996, 17, 744-757.
Chiari, M., et al. Electrophoresis 1994, 15, 177-186.
Gelfi, C., et al. Electrophoresis 1996, 17, 738-743.
Albarghouthi, M., Barron, A. E. Electrophoresis 2000, 21, 4096-4111.
Madabhushi, R. S., et al. Electrophoresis 1997, 18, 104-111.
Madabhushi, R. S., et al. Electrophoresis 1998, 19, 224-230.
Duke, T., et al. Biopolymers 1994, 34, 239-247.
Cottet, H., et al. Electrophoresis 1998, 19, 2151-2162.

* cited by examiner

*Primary Examiner*—Robert D. Harlan
(74) *Attorney, Agent, or Firm*—Casimir Jones, S.C.

(57) ABSTRACT

The present invention is generally directed to novel polymeric materials for use in the electrophoretic separation of nucleic acids. In particular, the novel polymer materials are sparsely crosslinked nanogels, dissolved in an aqueous buffer to form solutions with moderate to high viscosity. The present invention further provides methods for generating such novel polymers, and related methods of their use.

14 Claims, 20 Drawing Sheets

Linear polymer                Sparsely crosslinked "nanogel"

Linear polymer solution
(entangled)                Nanogel solution (entangled)

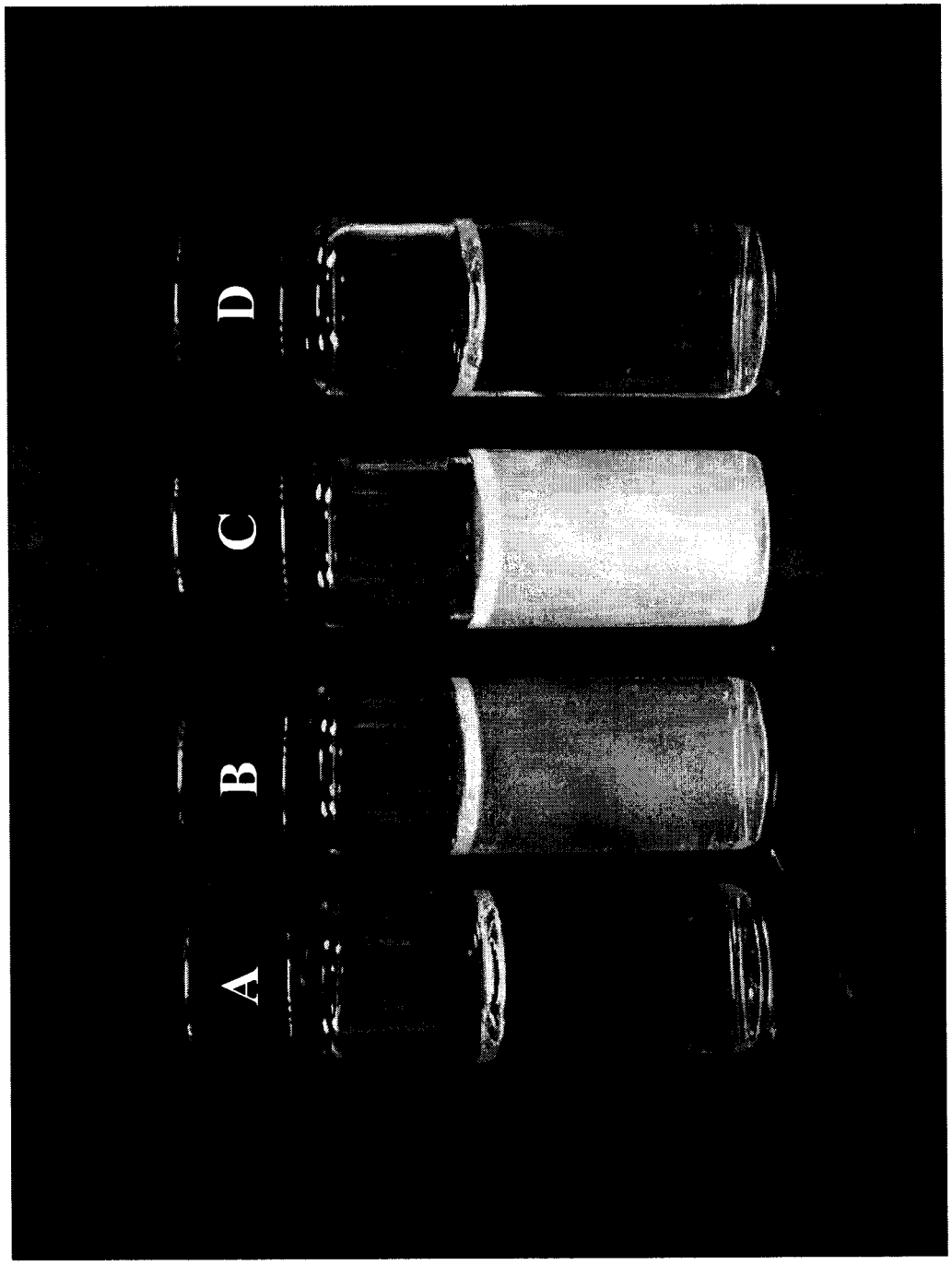

SEQUENCE LISTING

<160> NUMBER OF SEQ ID NOS: 2

<210> SEQ ID NO 1
<211> LENGTH: 697
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t

<400> SEQUENCE: 1

```
tctagtgcaa gcttgcatgc atgcaggtcg actctagagg ntccccgggt acgagctcga      60
attcgtaatc atggtcatag ctgtttcctg tgtgaaattg ttatccgctc acaattccac     120
acaacatacg agccggaagc ataaagtgta aagcctgggg tgcctaatga gtgagctaac     180
tcacattatt gcgttgcgct cactgcccgc tttccagtcg ggaaacctgt cgtgccagct     240
gcattaatga atcggccaac gcgcggggga gaggcggttt gcgtattggg cgccagggtg     300
gttttctttt tcaccagtga cgggcaaca agctgattgc cttcaccgcc tggcccctga     360
gagagttgca gcaagcggtc cacctgtttg ccccagcagg cgaaaatcct gtttgatggg     420
tggttccgaa atcggcaaaa atccttataa atcaaaaaga aataggcccg agatagggtt     480
gaagtggttg gtttccaagt tttgggaaag aagtccaact attaaaagga aacgtttggg     540
acttccaaac cggtcaaaag ggtgcgaata accggttct taatcaaggg gccgattggc     600
cacttacgt tggataccct attccacgca gaattcnag ttttttttg gggttcgaag      660
tttcccgtta anaggcctaa aattcggacc cctagag                             697
```

<210> SEQ ID NO 2
<211> LENGTH: 718
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t

<400> SEQUENCE: 2

```
catgcagctt gcatgctgca ggtcgactct agaggatccc gggtacgagc tcgaattcgt      60
aatcatggtc atagctgttt nnttgtgtga aattgttatc cgctcacaat tccacacaac     120
atacgagccg gaagcataaa gtgtaaagcc tggggtgcct aatgagtgag ctaactcaca     180
ttaattgcgt tgcgctcact gcccgctttc cagtcgggaa acctgtcgtg ccagctgcat     240
```

```
taatgaatcg gccaacgcgc ggggagaggc ggtttgcgta ttgggcgcca gggtggtttt    300
tcttttcacc agtgagacgg gcaacagctg attgccttca ccgcctggcc ctgagagagt    360
tgcagcaagc ggtccacctg gtttgcccca gcaggcgaaa atcctgtttg atggtggttc    420
cgaaatcggc aaaatccctt ataaatcaaa agaatagccc gagatagggt tgagtgttgt    480
tccagtttgg aaagagtcca ctattaaaga acgtggactc caacgtcaaa gggcgaaaaa    540
ccgtctatca gggcgatggc actacgtgaa ccatcaccca aatcaaagtt ttttggggtc    600
gaggtgccgt aaaagctaaa tcgggaacct aaaggagccc ccgatttaga gcttgaccgg    660
ganagccggc gaacgtggcg aganaggaat ggaaaaaagc ctaaaaggag ccgggcct     718
```

SPARSELY CROSS-LINKED NANOGELS: A NOVEL POLYMER STRUCTURE FOR MICROCHANNEL DNA SEQUENCING

This application is a Divisional of U.S. application Ser. No. 11/037,561, filed Jan. 18, 2005, which claims priority to U.S. Provisional Application Ser. No. 60/536,879, filed Jan. 16, 2004, both of which are hereby incorporated by reference in their entireties.

This invention was made with government support under NIH grant RO1 HG 019770-01. The United States government has certain rights in this invention.

FIELD OF THE INVENTION

The present invention is generally directed to novel polymeric materials for use in the DNA sequencing and other electrophoretic DNA separations such as for genotyping. In particular, the polymeric materials are sparsely crosslinked nanogels, dissolved in an aqueous buffer to form solutions with moderate to high viscosity. The present invention further provides methods for generating such novel polymeric nanogels, and related methods of use.

BACKGROUND

Capillary electrophoresis (CE) of DNA through polymeric separation matrices is presently the dominant technology for high-throughput sequencing. Although a final draft of the Human Genome was published recently (see, e.g., Marshall, E. Science 2000, 288, 2294-2295; Smaglik, P. Nature 2000, 404 (6774), 111-111; each herein incorporated by reference in their entireties), hundreds of other genome projects (see, e.g., Bernal, A., et al. Nucleic Acids Research 2001, 29 (1), 126-127; herein incorporated by reference in its entirety), as well as individualized genomics, still require long DNA sequencing read lengths at low cost. Novel polymeric matrices that provide longer read lengths than commercially available sequencing matrices will be instrumental for the throughput increases and cost reductions that are still required to make the long-term goal of personalized genomics economically feasible. In the present application, the inventors have developed a novel material for DNA sequencing with the clear potential to combine the high-selectivity separations of a crosslinked slab gel with the replaceable nature of a separation matrix composed of linear polymers.

Originally, DNA sequencing was performed on highly crosslinked polyacrylamide slab gels (see, e.g., Chrambach, A., Rodbard, D. Science 1971, 172, 440-450; Bishop, D. H., et al. Journal of Molecular Biology 1967, 26 (3), 373; each herein incorporated by reference in their entireties). Crosslinked polyacrylamide yields excellent DNA separations, allowing for long reads under optimized conditions (see, e.g., Ansorge, W., et al. Electrophoresis 1992, 13 (9), 616-619; herein incorporated by reference in its entirety). However, unless very low electric fields are used (which translates into long run times, typically 5-8 hours), large DNA sequencing fragments (>300 bases) rapidly enter the "biased reptation with orientation" (see, e.g., Slater, G. W., Noolandi, J. Biopolymers 1986, 25, 431-454; herein incorporated by reference in its entirety) migration mode in these highly crosslinked media. The process of obtaining long DNA sequencing reads using ultra-thin slab gels is time and labor intensive. For this reason, high-throughput genome sequencing centers largely abandoned slab gels in the late 1990s, in favor of automated capillary array electrophoresis (CAE) (see, e.g., Cheng, J. Prog. Biochem. Biophys. 1995, 22 (3), 223-227; herein incorporated by reference in its entirety).

During the initial stages of the development of capillary electrophoresis (CE), researchers used in situ-polymerized, highly crosslinked polyacrylamide within the lumen of the capillary. Sequencing in crosslinked polyacrylamide capillary gels was shown by Karger and co-workers (see, e.g., Heiger, D. N., et al. Chromatogr. 1990, 33-48; Cohen, A. S., et al. Journal of Chromatography 1990, 516 (1), 49; Guttman, A., et al. Anal. Chem. 1990, 62 (2), 137-141; each herein incorporated by reference in their entireties), Dovichi and co-workers (see, e.g., Harke, H. R., et al. J. Chromatogr. 1992, 608, 143-150; herein incorporated by reference in its entirety), Smith and co-workers (see, e.g., Smith, L. M. Nature 1991, 349 (6312), 812-813; Drossman, H., et al. Analytical Chemistry 1990, 62 (9), 900-903; Luckey, J. A., et al. Nucleic Acids Research 1990, 18 (15), 4417-4421; each herein incorporated by reference in their entireties), and Baba et al. (see, e.g., Baba, Y., et al. Anal. Chem. 1992, 64 (11), 1221-1225; herein incorporated by reference in its entirety) for sequencing reads of up to 350 bases. Crosslinked polyacrylamide capillary gels were typically produced using a total monomer concentration of up to 5% and a concentration of Bis up to 5%; short-read sequencing separations typically required 60-70 minutes.

The direct transfer of a "slab gel" technology to the micron-sized channels typical of fused-silica capillaries was not effective for a variety of reasons. First, voids left within the capillary due to the increased density of the polymer relative to its monomer are detrimental to highly efficient separations (see, e.g., Guttman, A., et al. Anal. Chem. 1990, 62 (2), 137-141; Bae, Y. C., et al. J. Chromatogr. A 1993, 652, 17-22; each herein incorporated by reference in their entireties). Second, an in situ-polymerized, highly crosslinked structure is difficult to remove from the capillary, making these prepared capillaries useful for a small number of separations each. Finally, since there is no a priori knowledge of the final polymer properties, rigorous quality control is not possible for in situ-polymerized matrices.

The use of a replaceable DNA sequencing matrix, in particular a highly entangled solution of LPA, provided resolution of ssDNA fragments without the use of an infinitely crosslinked polymer network (see, e.g., Heiger, D. N., et al. Chromatogr. 1990, 33-48; Bae, Y. C., et al. J. Chromatogr. A 1993, 652, 17-22; each herein incorporated by reference in their entireties). A 6% solution of relatively low molar mass LPA (~1×10$^6$ g/mol) provided a read length of over 350 bases in close to 30 minutes, indicating that a highly crosslinked polymer network was not required for DNA sequencing within capillaries (see, e.g., Ruiz-Martinez, M. C., et al. Anal. Chem. 1993, 65, 2851-2858; herein incorporated by reference in its entirety). Also, compared to sequencing separations by CE using crosslinked gels, comparable sequencing reads could be achieved in a shorter time (i.e., with a higher field), since a more open network shifts the "biased reptation with orientation" threshold to larger DNA sizes (see, e.g., Slater, G. W., Noolandi, J. Biopolymers 1986, 25, 431-454; herein incorporated by reference in its entirety).

Importantly, the use of physically entangled, linear polymer solutions for the separation of DNA sequencing fragments within capillaries also allowed for relatively facile loading and replacement of the separation matrix between runs (see, e.g., Ruiz-Martinez, M. C., et al. Anal. Chem. 1993, 65, 2851-2858; herein incorporated by reference in its entirety). This enabled, for the first time, complete automation of DNA sequencing. Moreover, production and characterization of polymers ex situ has allowed researchers to correlate polymer physical and chemical properties, including weight-average molar mass (see, e.g., Goetzinger, W., et al. Electrophoresis 1998, 19, 242-248; herein incorporated by reference in its entirety), polydispersity (see, e.g., Barron, A. E., et al. Electrophoresis 1996, 17, 744-757; Salas-Solano, O., et al. Anal. Chem. 1998, 70 (19), 3996-4003; each herein incorporated by reference in their entireties), and hydrophobicity (see, e.g., Albarghouthi, M. N., et al. Electrophoresis 2001, 22, 737-747; Chiari, M., et al. Electrophoresis 1994, 15, 177-186; Gelfi, C., et al. Electrophoresis 1996, 17, 738-743; each herein incorporated by reference in their entireties), with DNA separation performance.

The chemical and physical properties of polymers used for microchannel DNA sequencing are important, as they control the time scale of polymer-polymer and polymer-DNA interactions within the entangled polymer network, which in turn influences the mechanism of DNA separation (see, e.g., Bae, Y. C., et al. J. Chromatogr. A 1993, 652, 17-22; herein incorporated by reference in its entirety). An ideal polymer matrix for DNA sequencing should be hydrophilic, physically and chemically stable under sequencing conditions, and relatively low in viscosity (during loading and replacement). Typically, high-molar mass polymers ($M_w > 2 \times 10^6$ g/mol) give the best performance because they form robust entangled networks (see, e.g., Albarghouthi, M., Barron, A. E. Electrophoresis 2000, 21, 4096-4111; herein incorporated by reference in its entirety).

A range of linear polymers have shown good utility for use in DNA sequencing, including linear polyacrylamide (LPA) (see, e.g., Carrilho, E., et al. Anal. Chem. 1996, 68 (19), 3305-3313; Zhou, H., et al. Anal. Chem. 2000, 72 (5), 1045-1052; each herein incorporated by reference in their entireties), poly(N,N-dimethylacrylamide) (PDMA) (see, e.g., Madabhushi, R. S., et al. Electrophoresis 1997, 18, 104-111; Madabhushi, R. S., et al. Electrophoresis 1998, 19, 224-230; each herein incorporated by reference in their entireties), poly(ethylene oxide) (PEO) (see, e.g., Fung, E. N., et al. Anal. Chem. 1995, 67 (13), 1913-1919; herein incorporated by reference in its entirety), poly(vinyl pyrrolidone) (PVP) (see, e.g., Gao, Q. F., et al. Anal. Chem. 1998, 70 (7), 1382-1388; herein incorporated by reference in its entirety), poly(N-hydroxyethylacrylamide) (polyDuramide™) (see, e.g., Albarghouthi, M. N., et al. Electrophoresis 2002, 23 (10), 1429-1440; herein incorporated by reference in its entirety), and copolymers of N,N-dimethylacrylamide (DMA) and N,N-diethylacrylamide (DEA) (see, e.g., Albarghouthi, M. N., et al. Electrophoresis 2001, 22, 737-747; Buchholz, B. A., et al. Anal. Chem. 2001, 73, 157-164; each herein incorporated by reference in their entireties). To date, high-molar mass LPA gives the best sequencing performance, able to produce a 1000-base read in about 1 hour (see, e.g., Salas-Solano, O., et al. Anal. Chem. 1998, 70 (19), 3996-4003; herein incorporated by reference in its entirety) and 1300 bases in 2 hours (see, e.g., Zhou, H., et al. Anal. Chem. 2000, 72 (5), 1045-1052; herein incorporated by reference in its entirety) with highly optimized polymer molar mass distribution, matrix formulation, sample preparation and clean-up, and base-calling algorithms.

The long reads demonstrated by Karger and co-workers using high-molar mass LPA were accomplished using blends of high and low molar mass LPA. The 1000-base read was performed in a matrix blend composed of 2.0 wt % $9 \times 10^6$ g/mol and 0.5 wt % $5 \times 10^4$ g/mol LPA (see, e.g., Salas-Solano, O., et al. Anal. Chem. 1998, 70 (19), 3996-4003; herein incorporated by reference in its entirety); 1300 bases were sequenced in a matrix blend composed of 2 wt % $1.7 \times 10^7$ g/mol and 0.5 wt % $2.7 \times 10^5$ g/mol (see, e.g., Zhou, H., et al. Anal. Chem. 2000, 72 (5), 1045-1052; herein incorporated by reference in its entirety). The inclusion of a low percentage of low-molar mass polymer increases the total polymer concentration of the matrix, allowing smaller ssDNA fragments to be separated without significantly decreasing the selectivity for the large ssDNA fragments provided by the highly entangled, high-molar mass polymer (see, e.g., Heller, C., et al. Electrophoresis 1999, 20, 1962-1977; Duke, T., et al. Biopolymers 1994, 34, 239-247; Cottet, H., et al. Electrophoresis 1998, 19, 2151-2162; each herein incorporated by reference in their entireties). Significantly shorter read lengths are common in commercial CAE instruments such as the ABI PRISM 3700™ (550 bases in 3-4 hours) and the MegaBACE 1000™ (600 bases in 2 hours), due to the use of lower-viscosity, less entangled matrices for practical reasons and the lower quality of actual genomic DNA samples, among other factors.

Polyacrylamide is a near-ideal polymer for DNA sequencing due to its high hydrophilicity, hence, its excellent ability to entangle with other polyacrylamide chains in aqueous solution, and its facile production to high molar mass using standard free-radical polymerization chemistry. Polyacrylamide is also relatively easy to purify, as it readily precipitates from water with the addition of acetone or methanol. A highly entangled LPA matrix suitable for long-read sequencing has an extremely high zero-shear viscosity (60,000-120,000 cP); hence, high pressure (i.e., 6895 kPa (1000 psi)) is required to initiate flow into the microchannel.

The use of branched copolymer structures for DNA sequencing matrices has been explored as a way to improve the performance of lower-molar mass LPA by modifying its network properties. Viovy and co-workers have produced a relatively low-molar mass, branched copolymer with a polyacrylamide backbone. Poly(acrylamide-g-N-isopropylacrylamide) (see, e.g., Sudor, J., et al. Electrophoresis 2001, 22, 720-728; herein incorporated by reference in its entirety), when heated above the lower critical solution temperature (LCST) of N-isopropylacrylamide (NIPA), forms micelle-like aggregates of NIPA grafts, stabilizing the branched polymer network with "transient crosslinks" and increasing the matrix viscosity by nearly two orders of magnitude (from 100 to 10,000 cP). This polymer displayed excellent utility for the separation of dsDNA in published work, but was not tested as a DNA sequencing matrix. Although this class of branched polymers improves the loading properties of LPA (since lower-molar mass, less viscous solutions can be used), they do not provide the highly entangled network presented by solutions of ultra-high molar mass LPA ($M_w > 9 \times 10^6$ g/mol) previously demonstrated by Karger and co-workers to give long read lengths.

Chemical crosslinks within slab gels produce an infinitely crosslinked separation medium and provide a mechanically stabilized pore structure for the migration of DNA. An abundance of crosslinks within a slab gel decreases the effective pore size and limits sample diffusion and dispersion during separation (see, e.g., Ugaz, V. M., et al. Electrophoresis 2002, 23 (16), 2777-2787; herein incorporated by reference in its entirety), which is desirable to produce narrow bands on the gel. Ideally, the presence of chemical crosslinks in a high-molar mass polymer for CE would provide the same benefits. Occasional crosslinks within a physically entangled matrix composed of high molar mass polyacrylamide should decrease sample diffusion as well as provide a more robust network for migrating DNA, allowing for significantly longer read lengths when compared to a commercially available linear polyacrylamide having a similar molar mass and extent of physical entanglements.

Two major challenges exist when attempting to incorporate crosslinks into a polymer to be used as a sequencing matrix for CAE. First, the formation of an infinitely crosslinked polymer gel during the polymerization process should be avoided. In addition, large polymer structures of colloidal dimensions should be avoided, as these particles would scatter incident light, preventing sequencing using LIF detection. Finally, the crosslink density should be limited so that the final sequencing matrix retains good fluidity, and so that individual polymer structures may physically entangle with each other (see FIG. 1).

SUMMARY OF THE INVENTION

The present invention is generally directed to novel polymeric materials for use in electrophoretic separation of nucleic acids, such as DNA sequencing or the size-based separation of DNA molecules for other applications, including forensic genotyping or the determination of genetic alterations for medical or biotechnology research purposes. In particular, the novel polymeric materials are sparsely crosslinked nanogels, dissolved in an aqueous buffer to form solutions of moderate to high viscosity. The present invention further provides methods for generating such novel polymeric nanogel materials, and related methods of their use.

In exemplary embodiments, the invention provides a spherical nanogel composition comprising a sparsely cross-linked polymer structure, wherein the nanogel is formed from the polymerization of a water-soluble monomer typically used in the formation of DNA sequencing polymers, and the polymer also comprises a water-soluble monomer cross-linked by from about $1\times10^{-8}$ mol % to about $1\times10^{-3}$ mol % non-ionic, hydrophilic cross-linking moiety as compared to the amount of water-soluble monomer present. It is contemplated that the nanogels of the invention may be formed from monomers that are all of one type or alternatively formed from the co-polymerization of two or more different monomers. Thus, another aspect of the present invention defines a spherical nanogel composition comprising a sparsely cross-linked polymer, wherein the polymer is formed from the co-polymerization of two or more different water-soluble monomers used in the formation of DNA sequencing polymers, wherein the polymer comprises the water-soluble monomers cross-linked by from about $1\times10^{-8}$ mol % to about $1\times10^{-3}$ mol % non-ionic, hydrophilic cross-linking moiety as compared to the amount of water-soluble monomer present. While the present application provides that the nanogels are preferably spherical, it should be understood that the nanogels need not necessarily be spherical.

As discussed herein, the monomers used for the polymer nanogels may be any monomer typically used for the formation of a sequencing gel. Simply by way of example, such monomers include, but are not limited to, acrylamide, N,N-dimethylacrylamide, ethylene oxide, N-hydroxy ethylacyrlamide, N-ethoxyethylacrylamide, and N-methoxyethylacrylamide. Co-polymers of two or more of these monomers are particularly contemplated. In certain embodiments, it is contemplated that the use of one or more thermoresponsive monomers (e.g., N,N-diethylacrylamide or methoxyethyl acrylamide) may be particularly useful. In preferred embodiments, the water-soluble monomer is acrylamide.

The polymers of the invention may be cross-linked with any non-ionic, hydrophilic cross-linker. Exemplary cross-linkers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethylene glycol diacrylate, ethylene glycol methacrylate, 1,6-hexanediol diacrylate, 1,6-hexanediol dimethylacrylate, neopentyl glycol dimethylacrylate, polyethylene glycol diacrylate, polyethylene glycol dimethylacrylate, tryethylene glycol diacrylate, tryethylene glycoldimethylacrylate, tripropylene glycol diacrylate, tetraethylene glycol diacrylate, tetraethylene glycol dimethylacrylate, divinyl esters of a polycarboxylic acid, diallyl esters of a polycarboxylic acid, diallyl maleate, diallyl fumarate, hexamthylenebismaleimide, divinyl adipate, diallyl succinate, a divinyl ether of ethylene glycol, cylcopentadiene diacrylate, N,N'-methylenebisacrylamide, N,N'-methylenebismethacrylamide, ethylene glycol dimethylacrylate and mixtures thereof. In particularly preferred embodiments, the cross-linker is N,N'-methylenebisacrylamide, N,N'-methylenebismethacrylamide or a mixture of N,N'-methylenebismethacrylamide and N,N'-methylenebisacrylamide. Mixtures of other cross-linkers also are contemplated.

In preferred embodiments of the present invention, the nanogel is composed of polymers of the monomer acrylamide cross-linked by N,N'-methylenebisacrylamide. Other preferred embodiments, contemplate a nanogel composed of polymers of acrylamide cross-linked by a mixture of N,N'-methylenebisacrylamide and N,N'-methylenebismethacrylamide.

In specific embodiments, the hydrophilic cross-linking moiety preferably is present in an amount of about $1\times10^{-8}$ mol % as compared to amount of water-soluble monomer present. Other embodiments, prefer that the hydrophilic cross-linking moiety is present in an amount of about $1\times10^{-7}$ mol % as compared to amount of water-soluble monomer present. Still further preferred embodiments contemplate that the hydrophilic cross-linking moiety is present in an amount of about $1\times10^{-6}$ mol % as compared to amount of water-soluble monomer present. Yet other embodiments contemplate that the hydrophilic cross-linking moiety is present in an amount of about $1\times10^{-5}$ mol % as compared to amount of water-soluble monomer present. Still other embodiments have a hydrophilic cross-linking moiety present in an amount of about $1\times10^{-4}$ mol % as compared to amount of water-soluble monomer present or in an amount of about $1\times10^{-3}$ mol % as compared to amount of water-soluble monomer present. It should be noted that these preferred embodiments merely provide exemplary amounts of the cross-linker, and those of skill in the art would understand that any individual numerical amount between about $1\times10^{-8}$ mol % to about $1\times10^{-3}$ mol % non-ionic, hydrophilic cross-linking moiety is particularly contemplated and each of the individual values between this range is specifically intended to be within the scope of the invention, and each individual value between this range has not been recited simply for ease of legibility and not because it was intended to be excluded from the scope of the application.

The nanogels of the invention may be defined by the property of viscosity of their aqueous solutions. It is contemplated that the nanogel composition of the invention has a low shear viscosity of from about 300 centipoise to about 200,000 centipoise when the polymer is dissolved in an aqueous buffer (e.g., 1×TTE buffer, or 1×TBE buffer, or another aqueous buffer commonly used for microchannel electrophoresis of DNA). The term "low shear" is intended to refer to an applied shear rate of less than 0.1 sec$^{-1}$. In preferred embodiments, the nanogel solution has a low shear viscosity of from about 1,000 centipoise to about 120,000 centipoise when the polymer is dissolved in an aqueous buffer. In other embodiments the preferred low shear viscosity is about 10,000 centipoise when the polymer is dissolved in an aqueous buffer. Other embodiments contemplated a low shear viscosity of about 10,000 centipoise when the polymer is dissolved in an aqueous buffer. As with the range of cross-linker, the range of viscosity recited herein is intended to include and specifically incorporates all values between 300 centipoise to about 200,000 centipoise.

In preferred embodiments, the sparsely cross-linked polymeric structures having average radii of nanoscale dimensions (i.e., the nanogels) of the invention is one which is formed using inverse emulsion polymerization. The term inverse emulsion polymerization is well known to those of skill in the art, and any such technique used for the polymerization of e.g., acrylamide is intended to be useful herein.

Another aspect of the invention describes a method of making a sparsely cross-linked polymer structure, the method comprising: obtaining an emulsion of isoparaffin and sorbitan monoleate; adding to the emulsion a mixture of a water-soluble monomer used in formation of DNA sequencing polymers and water; adding an aqueous solution of difunctional monomer to the mixture, wherein the aqueous solution of difunctional monomer comprises between about $1 \times 10^{-8}$ mol % to about $1 \times 10^{-3}$ mol % difunctional monomer as compared to the amount of water-soluble monomer present; and polymerizing the resultant mixture.

The method may preferably use acrylamide as the monomer. In preferred embodiments the polymerizing comprises adding a polymerization catalyst and a polymerization initiator to the mixture. Preferably, the catalyst is N,N,N',N' tetraethylmethylenediamine. The polymerization initiator may be any polymerization initiator, including but not limited to ammonium persulfate and 2,2'-azobisisobutyronitrile. The method of making the sparsely cross-linked polymer may further comprise precipitating the polymerized product in methanol or acetone.

Another aspect of the invention is directed to a method of forming a nanogel-filled capillary useful for electrophoresis comprising the steps of providing a capillary; providing a polymerized nanogel of the invention; and filling the capillary with the polymerized product. Preferably, the monomer is acrylamide and the gel is composed of between 2% and 10% acrylamide and comprises a molar percentage of from about $1 \times 10^{-7}$ mol % to about $1 \times 10^{-5}$ mol % cross-linker as compared to the amount of monomer present. In specific embodiments, the cross-linker is methylenebisacrylamide.

A further aspect of the invention describes a method of separating a sample into its molecular species comprising polymerizing a polymerizable monomer and a cross-linker present in a molar percentage of from about $1 \times 10^{-7}$ mol % to about $1 \times 10^{-5}$ mol % cross-linker as compared to the amount of monomer present into a nanogel; applying the sample to be separated with the nanogel; performing electrophoresis on the sample to separate the sample into its constituent molecular species. The sample is preferably a sample of nucleic acid (e.g., DNA). In more particular embodiments, the sample comprises single stranded DNA (ssDNA). In other embodiments, the sample comprises double-stranded DNA. In further embodiments, the method further comprises detecting the separated products detecting the separated products. In particularly preferred embodiments, the ssDNA moieties range from 1 base to about 1300 bases of DNA. In other specific embodiments, the nanogel-based polymer matrix comprises about 3% (w/v) polymer in an aqueous solution, more particularly, the nanogel matrix has a composition comprising 2.75% polymer in aqueous solution.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

The following drawings form part of the present specification and are included to further illustrate aspects of the present invention. The invention may be better understood by reference to the drawings in combination with the detailed description of the specific embodiments presented herein.

FIG. 17 shows polyDEA and DEA/DMA (40%/60%, w/w) nanogels dissolved in water at different concentrations from left to right (a) DEA/DMA nanogels (8 wt %), (b) polyDEA nanogels (6 wt %), (c) polyDEA nanogels (1 wt %), (d) DEA/DMA nanogels (1 wt %).

DETAILED DESCRIPTION OF THE INVENTION

The present invention is generally directed to novel polymeric materials for use in DNA sequencing and other types of electrophoresis-based genetic analyses relying on a size-based separation of DNA molecules. In particular, the novel polymeric materials are sparsely crosslinked nanogel structures which, when dissolved in an aqueous solution, form matrices with moderate to high viscosity. The present invention further provides methods for generating such novel polymeric nanogel materials, and related methods of their use. Exemplary embodiments of the present invention are described below.

I. Sparsely Cross-Linked Nanogel Matrices

Figure 1:
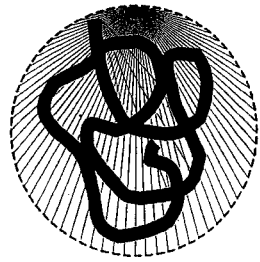
FIG. 1 shows a schematic representation of nanogels (right) and linear polymer chains (left). Nanogels entangle with each other, forming a network similar to a solution of entangled linear polymer, but stabilized by the presence of chemical crosslinks. Note that while each nanogel has an internally, sparsely crosslinked structure, there are not crosslinks that link one nanogel domain to another; this is a preferred aspect of the invention. In preferred embodiments, since the crosslinked nanogel domains are not covalently bonded to one another, the nanogel solution is still quite fluid, similar to a solution of linear polymers. However, as shall be discussed, the inclusion of the crosslinks endows these nanogel solutions with distinct and advantageous properties for electrophoretic DNA separations in capillaries and chip-based microchannels.
Figure 1:
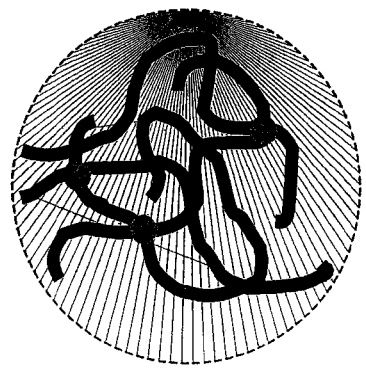
Figure 1:
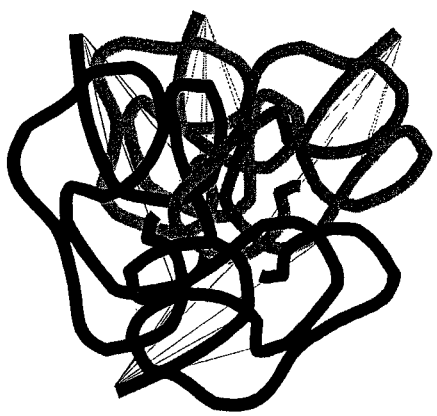
Figure 1:
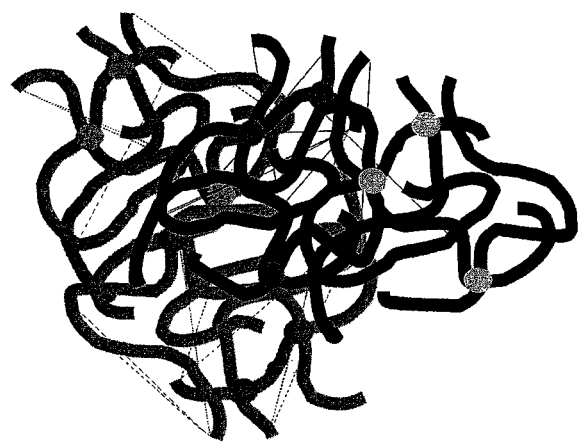

The polymeric materials presently which were originally in matrices for the electrophoretic separation of nucleic acids were are inadequate because they comprised a large degree of crosslinking and the presence of an infinitely crosslinked polymer gel during the polymerization process produces a gel that does not have the desired fluidity. In addition, the presence of large polymer structures (e.g., diameter >1 micrometer) in the crosslinked polymers could lead to the scattering of incident light, preventing sensitive DNA detection using laser induced fluorescence. Finally, the crosslink density should be limited and the crosslinking should be localized to discrete polymer domains, so that the final separation matrix is not "infinitely" crosslinked and so retains good fluidity, and so that individual polymer structures may physically entangle with each other (see FIG. 1).

To fulfill these requirements, the present application provides, for example, the production of sparsely crosslinked "nanogels" using inverse emulsion polymerization (e.g., polymerization within small water droplets stabilized by surfactant within an organic medium). Inverse emulsion polymerization of acrylamide and other water-soluble monomers is a common method for the production of highly crosslinked, monodisperse latex particles (see, e.g., Arshady, R., Colloid Polym. Sci. 1992, 270 (8), 717-732; herein incorporated by reference in its entirety) as well as high-molar mass linear polymer (see, e.g., Hunkeler, D., Polym. Int. 1992, 27 (1), 23-33; Hunkeler, D. J., Macromolecules 1991, 24 (9), 2160; Baade, W., Reichert, K. H., Eur. Polym. J. 1984, 20, 505-512; each herein incorporated by reference in their entireties). Advantages of inverse emulsion polymerization over solution polymerization include isolation of the domains of chemical reaction, better temperature control, relatively low polydispersity of the polymer product, and low-viscosity reaction products containing a high mass fraction of polymer (e.g., 20-40 wt %). Karger and co-workers have used this approach to produce high-molar mass, non-crosslinked, LPA for DNA sequencing (see, e.g., Goetzinger, W., et al. Electrophoresis 1998, 19, 242-248; Salas-Solano, O., et al. Anal. Chem. 1998, 70 (19), 3996-4003; Zhou, H., et al. Anal. Chem. 2000, 72 (5), 1045-1052; each herein incorporated by reference in their entireties).

The sparsely crosslinked nanogels described herein occupy a new middle ground, between the highly crosslinked, in situ-produced polyacrylamide capillary gels and the fluid, linear polymer networks that are now utilized for CAE. As described in further detail below, nanogels comprised of the sparsely cross-linked polymers of the present invention were characterized by batch multi-angle laser light scattering (MALLS), steady-shear and oscillatory shear rheometry, and tested as DNA sequencing matrices. The following disclosure demonstrates that stabilization of a physically entangled separation matrix is possible by including an extremely small amount of difunctional monomer, which provides chemical crosslink points that fortify the final entangled polymer network and improve separation results.

The term "nanogel," as used herein refers to a discrete polymer structure not physically or covalently linked to other polymer structure, wherein the discrete polymer structure has a radius in size range of 50 nm to 350 nm and which contains cross-linked both between and within polymer chains such that upon infinite dilution the nanogel retains its structure and links numerous polymer chains together. Due to these distinct features, the polymer structure when dissolved in e.g., an aqueous, electrophoresis buffer forms an entangled, but not an infinitely cross-linked network. The present invention is not limited to a particular mechanism. Indeed, an understanding of the mechanism is not necessary to practice the present invention. Nonetheless, this ability to form an entangled, but not infinitely cross-linked network is important for the retention of the fluidity of the polymer network and distinguishes the entangled nanogel network of the present invention from any polymer structure previously identified as useful for nucleic acid separations. The amount of cross-linker in such nanogels is low, e.g., preferably less than $10^{-3}$ mol % relative to the amount of water-soluble monomer. More heavily cross-linked nanogels are produced when higher amounts (e.g., greater than 0.1 mol % relative to the amount of water-soluble monomer present) do not retain the desired fluidity for microchannel loading.

Typical exemplary nanogels of the invention are formed using inverse emulsion (e.g., water-in-oil) copolymerization of acrylamide and a low percentage (e.g., ~$10^{-4}$ mol %) of N,N-methylene bisacrylamide (Bis). Such exemplary nanogels have an average radius of ~230 nm, with ~75% of chains incorporating a Bis cross-linker.

Thus, the present application demonstrates the development and utility of a novel class of polymer structures to be used as a chemically stabilized, flowable matrix for nucleic acid separation. This new polymer structure allows for the stabilization of the matrix through the introduction of occasional chemical crosslinks, while still allowing automated, high-throughput microchannel DNA sequencing that is currently being carried out using uncrosslinked, physically entangled, linear polymer solutions. Currently, there are no other nucleic acid matrices commercially available that utilize non-linear polymers.

In comparison to a commercially available linear polyacrylamide matrix, the matrices described herein, as composed of nanogels having a similar weight-average molar mass to the commercial polymer, provide at least a 10.4% increase in average read length at 98.5% accuracy and a 6.7% increase in average read length at 98% accuracy (described in more detail below). Some optimized formulations also discussed below provided an 18% longer DNA sequencing read length as compared to an LPA of similar average molar mass and with a similar extent of entanglement. In addition, for ssDNA longer than approximately 300 bases, nanogel matrices provide a more selective separation than matrices composed of linear polymer (described in more detail below). Nanogel matrices provide substantially longer read lengths using approximately 30% less polymer per unit volume of sequencing matrix than commercially available DNA sequencing matrices composed of linear polymers (described in more detail below).

Moreover, nanogel matrices require 30% less polymer per unit volume than LPA. The addition of a small amount of low-molar mass LPA or ultra-high-molar mass LPA to the optimized nanogel sequencing matrix further improves read length as well as the reproducibility of read length (e.g., RSD <1.6%).

The use of a sparsely crosslinked polymer structure is a novel way to combine the advantageous properties of an infinitely chemically crosslinked network (e.g., matrix stability to migrating DNA) and the properties of a physically entangled linear polymer matrix (flowability and a priori knowledge of polymer physical properties). Further it is contemplated that the sparsely crosslinked polymer structure also may be used for oil recovery and other viscosifying applications, because the sparsely crosslinked polymer is a flowable polymer solution that does not shear-thin as extensively as linear polymer solutions.

Methods and compositions for making, testing and using the sparsely cross-linked polymers of the present invention are described in further detail herein below. In particular, it is noted that the matrices of the invention allow >680-base read lengths in a chip-based sequencing system, in an analysis time of <30 minutes. The nanogels of the present invention outperform an appropriately matched LPA matrix and can be easily replaced between each DNA sequencing run.

While the above description is presented in terms of forming a sparsely crosslinked polymer of acrylamide and N-methylene bisacrylamide, using N-methylene bisacrylamide as the crosslinking moiety, it should be understood that those of skill in the art will be able to use any crosslinker. Particularly preferred crosslinkers include those that are non-ionic and hydrophilic. Examples of such crosslinkers include polyvinyl monomers including, but not limited to, polyacrylic (or polymethacrylic) acid esters presented by formula (I) below and bisacrylamides represented by formula (III) below:

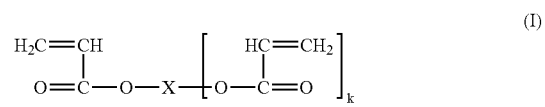

wherein x is ethylene, propylene, trimethylene, cyclohexyl, hexamethylene, 2-hydroxypropylene, —(CH$_2$CH$_2$O)$_n$CH$_2$CH$_2$— or

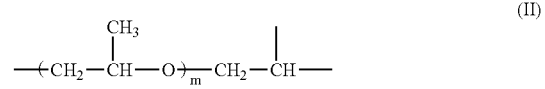

n and m are each an integer 5 to 40, and k is 1 or 2;

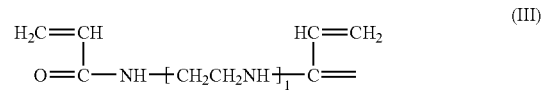

wherein 1 is 2 or 3.

The compounds of formula (III) are prepared by reacting polyols such as ethylene glycol, propylene glycol, trimethylolpropane, 1,6-hexanediol, glycerin, pentaerythritol, polyethylene glycol or polypropylene glycol, with acrylic acid or methacrylic acid. The compounds of formula (III) are obtained by reacting polyalkylene polyamines, such as diethylenetriamine and triethylenetriamine, with acrylic acid.

Specific crosslinking monomers that may be used herein include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethylene glycol diacrylate, ethylene glycol methacrylate, 1,6-hexanediol diacrylate, 1,6-hexanediol dimethylacrylate, neopentyl glycol dimethylacrylate, polyethylene glycol diacrylate, polyethylene glycol dimethylacrylate, tryethylene glycol diacrylate, tryethylene glycoldimethylacrylate, tripropylene glycol diacrylate, tetraethylene glycol diacrylate, tetraethylene glycol dimethylacrylate, divinyl esters of a polycarboxylic acid, diallyl esters of a polycarboxylic acid, diallyl maleate, diallyl fumarate, hexamthylenebismaleimide, divinyl adipate, diallyl succinate, a divinyl ether of ethylene glycol, cylcopentadiene diacrylate or mixtures thereof. Especially preferred crosslinking agents are N,N'-methylenebisacrylaminde, N,N'-methylenebismethacrylaminde, and ethylene glycol dimethylacrylate.

The polymers of the present invention may be made, for example, by incorporating crosslinking moieties into linear polymers that are commonly used for DNA sequencing, including linear polyacrylamide (LPA) (see, e.g., Carrilho, E., et al. Anal. Chem. 1996, 68 (19), 3305-3313; Zhou, H., et al. Anal. Chem. 2000, 72 (5), 1045-1052; each herein incorporated by reference in their entireties), poly(N,N-dimethylacrylamide) (PDMA) (see, e.g., Madabhushi, R. S., et al. Electrophoresis 1997, 18, 104-111; Madabhushi, R. S., et al. Electrophoresis 1998, 19, 224-230; each herein incorporated by reference in their entireties), poly(ethylene oxide) (PEO) (see, e.g., Fung, E. N., et al. Anal. Chem. 1995, 67 (13), 1913-1919; herein incorporated by reference in its entirety), poly(ethylene oxide) (PVP) (see, e.g., Gao, Q. F., et al. Anal. Chem. 1998, 70 (7), 1382-1388; herein incorporated by reference in its entirety), poly(N-hydroxyethylacrylamide) (polyDuramide™) (see, e.g., Albarghouthi, M. N., et al. Electrophoresis 2002, 23 (10), 1429-1440; herein incorporated by reference in its entirety), and copolymers of N,N-dimethylacrylamide (DMA) and N,N-diethylacrylamide (DEA) (see, e.g., Albarghouthi, M. N., et al. Electrophoresis 2001, 22, 737-747; Buchholz, B. A., et al. Anal. Chem. 2001, 73, 157-164; each herein incorporated by reference in their entireties). In the preferred embodiments, the crosslinked polymers are produced from polyacrylamide, however it is contemplated that the other DNA sequencing polymers may also be advantageously crosslinked using inverse emulsion polymerization as exemplified herein above for the sparsely crosslinked polymer of acrylamide and Bis.

As discussed herein above, the polymeric nanogel materials of the present invention are sparsely cross-linked. The term "sparsely cross-linked" is governed by the amount of cross-linking agent present in the cross-linked polymers. In preferred embodiments, the cross-linking agent is present in an amount of from about $1 \times 10^{-8}$ mol % to about $1 \times 10^{-3}$ mol % of the total number of moles of monomer present in the polymer. Preferably, the cross-linking agent is present in a molar percentage of from $1 \times 10^{-7}$ mol % to about $1 \times 10^{-4}$ mol %. Most preferably, the cross-linking agent is present in a molar percentage of from about $1 \times 10^{-6}$ mol % to about $1 \times 10^{-5}$ mol %. It is particularly contemplated that the sparsely cross-linked polymer comprises not more than 0.1%.

The nanogels of the present invention which comprise extremely low amounts of cross-linker may be used in any electrophoresis methods known to those of skill in the art. For additional disclosure electrophoresis methods that the gels of the present invention may be used in, those of skill in the art are referred to e.g., U.S. Pat. Nos. 5,332,481, 5,370,777, 5,213,669, 5,421,980, 5,296,116, each of which is specifically incorporated herein by reference in its entirety. The nanogel-based polymer solutions of the present invention could be used for DNA sequencing and/or DNA separation according to DNA size or DNA conformation in any electrophoresis system that uses channels of microscale diameter including, but not limited to, capillary and microfluidic chip systems.

II. Thermoresponsive Nanogels

Nanogels, (e.g., hydrogel nanoparticles or microgels with diameters in the range of tens to hundreds of nanometers) have attracted significant interest of late (see, e.g., Sakai, T., Yoshida, R. Langmuir 2004, 20, 1036; Jones, C., Lyon, A. Macromolecules 2003, 36, 1988; Lu, X., Hu, Z., Gao, J. Macromolecules 2000, 33, 8698; Pelton, R. Adv. Colloid Interface Sci. 2000, 85, 1; each herein incorporated by reference in their entireties). Relative to bulk hydrogels and due to their very small size, nanogels can show an unusually rapid response to microenvironmental stimuli such as temperature (see, e.g., Jones, C., Lyon, A. Macromolecules 2003, 36, 1988; herein incorporated by reference in its entirety) and pH (see, e.g., Zhou, S., Chu, B. J. Phys. Chem. B 1998, 102, 1364; herein incorporated by reference in its entirety). These polymeric nanoparticles have found important applications in numerous areas of controlled drug release (see, e.g., McAllister, K.; Sazani, P.; Adam, M.; Cho, M.; Rubinstein, M.; Samulski, R.; DeSimone, J. JACS 2002, 124, 15198; Vinogradov, S.; Batrakova, E.; Kabanov, A. Bioconjugate Chem. 2004, 15, 50; each herein incorporated by reference in their entireties), biotechnology (see, e.g., Tabuchi, M.; Ueda, M.; Kaji, N.; Yamasaki, Y.; Nagasaki, Y.; Yoshikawa, K.; Kataoka, K.; Baba, Y. Nature Biotechnology 2004, 22, 337; herein incorporated by reference in its entirety), and environmental control (see, e.g., Morris, G.; Vincent, B.; Snowden, M. J. Colloid Interface Sci. 1997, 190, 198; herein incorporated by reference in its entirety), as well as optical applications (see, e.g., Serpe, M.; Kim, J.; Lyon, A. Advanced Materials 2004, 16, 184; Reese, C.; Mikhonin, A.; Kamenjicki, M.; Tikhonov, A.; Asher, S. JACS 2004, 126, 1493; each herein incorporated by reference in their entireties). Recently, thermo-responsive nanogels (see, e.g., Pelton, R. Adv. Colloid Interface Sci. 2000, 85, 1; Ogawa, K.; Nakayama, A.; Kokufuta, E. Langmuir 2003, 19, 3178; each herein incorporated by reference in their entireties) have been created and studied that exhibit a reversible volume-phase transition (VPT) at a given volume-phase transition temperature (VPTT). Below the VPTT, the polymer chains in each nanogel form hydrogen bonds with water and the nanogels swell in aqueous media. Above the VPTT, polymer chains in each nanogel shrink due to polymer-polymer hydrophobic association. The micro-phase separation and effective shrinking of the polymer chains leads to a precipitous volume collapse of the nanogels at temperatures above the VPTT.

Among various thermo-responsive poly(N-alkyl substituted acrylamide) nanogels (see, e.g., Pelton, R. Adv. Colloid Interface Sci. 2000, 85, 1; Lowe, J., Chowshry, B., Parsonage, J., Snowden, M. Polymer 1998, 39, 1207; Duracher, D.; Elaissari, A.; Pichot, C. J. Polym. Sci., Part A Polym. Chem. 1999, 37, 311; each herein incorporated by reference in their entireties), poly(N-isopropylacrylamide) (polyNIPA) nanogels have been the most extensively investigated (see, e.g., Gan, D.; Lyon, A. JACS 2001, 123, 8203; Kazakov, S.; Kaholek, M.; Teraoka, I.; Levon, K. Macromolecules 2002, 35, 1911; Ogawa, K.; Nakayama, A.; Kokufuta, E. J. Phys. Chem. B 2003, 107, 8223; Oh, K.; Oh, J.; Choi, H.; Bae, Y. Macromolecules 1998, 31, 7328; each herein incorporated by reference in their entireties). NIPA-based nanogels are usually synthesized by emulsion precipitation polymerization at 70° C. (see, e.g., Berndt, I.; Richtering, W. Macromolecules 2003, 36, 8780; herein incorporated by reference in its entirety). Similar to linear polyNIPA chains, polyNIPA nanogels exhibit a reversible volume phase transition at a VPTT of 32° C. Below the VPTT, the swollen polyNIPA nanogels are stable in solution due to a low effective Hamaker constant (see, e.g., Pelton, R. Adv. Colloid Interface Sci. 2000, 85, 1; Bregstrom, L. Adv. Colloid Interface Sci. 1997, 70, 125; each herein incorporated by reference in their entireties). Above the VPTT, they can, in most cases, still remain stably dispersed, reportedly due to electrostatic repulsions between ammonium persulfate (APS) moieties incorporated into the nanogels (see, e.g., Pelton, R. Adv. Colloid Interface Sci. 2000, 85, 1; herein incorporated by reference in its entirety). The VPTT of NIPA-based nanogels has been varied by the incorporation of a small amount of an ionic comonomer such as acrylic acid (AA) (see, e.g., Ito, S.; Ogawa, K.; Suzuki, H.; Wang, B.; Yoshida, R.; Kokufuta, E. Langmuir 1999, 15, 4289; herein incorporated by reference in its entirety) or methacrylic acid (MAA) (see, e.g., Zhou, S., Chu, B. J. Phys. Chem. B 1998, 102, 1364; herein incorporated by reference in its entirety) these copolymer nanogels exhibit both temperature- and pH-induced volume-phase transitions.

In addition to polyNIPA, poly(N,N-diethylacrylamide) (polyDEA) is another widely studied thermo-responsive polymer. PolyDEA undergoes a reversible volume-phase transition at 25° C. (see, e.g., Taylor, L.; Cerankowski, L. J. Polym. Sci., Polym. Chem. Ed. 1975, 13, 2551; herein incorporated by reference in its entirety) or 33° C. (see, e.g., Idziak, I.; Avoce, D.; Lessard, D.; Gravel, D.; Zhu, X. Macromolecules 1999, 32, 1260; herein incorporated by reference in its entirety), depending on the synthesis conditions. Zhu and coworkers measured the VPTTs of various DEA-based copolymers (see, e.g., Liu, H.; Zhu, X. Polymer 1999, 40, 6985; herein incorporated by reference in its entirety), while Wu et al. investigated the effect of comonomer composition on the formation of the mesoglobular phase of DEA copolymers using laser light scattering technology (see, e.g., Siu, M.; Liu, H.; Zhu, X.; Wu, C. Macromolecules 2003, 36, 2103; herein incorporated by reference in its entirety). Barron et al. showed that the incorporation of the neutral hydrophilic comonomer DMA in random DMA/DEA copolymers leads to the shift of the VPTT to higher temperature (see, e.g., Buchholz, B.; Doherty, E.; Albarghouthi, M.; Bogdan, F.; Zahn, J.; Barron, A. Anal. Chem. 2001, 73, 157; herein incorporated by reference in its entirety). The ability to control the VPTT of these charge-neutral, thermo-responsive copolymers has important consequence in their applications (see, e.g., He, H.; Buchholz, B.; Kotler, L.; Miller, A.; Barron, A.; Karger, B. Electrophoresis 2002, 23, 1421; herein incorporated by reference in its entirety). For example, by exploiting the dramatic viscosity drop associated with the VPT of linear DEA/DMA copolymer solutions, Barron and coworkers (see, e.g., Buchholz, B.; Doherty, E.; Albarghouthi, M.; Bogdan, F.; Zahn, J.; Barron, A. Anal. Chem. 2001, 73, 157; herein incorporated by reference in its entirety) created novel microchannel DNA sequencing matrices with a thermally controlled "viscosity switch", capable of decoupling high-pressure microchannel matrix loading and DNA sequencing separation performance.

The development of polymeric matrices with "switchable viscosity" represents a strategy to decouple capillary loading and DNA separation properties, which opens the possibility of using glass/plastic microchips for high-throughput DNA sequencing. For example, "thermothinning" polymer networks undergo a thermodynamically driven volume-phase transition, accompanied by a dramatic decrease in viscosity, in response to a change in temperature over a narrow range. Exploiting the volume phase transition of thermo-responsive nanogels allows, for example, rapid matrix loading into a capillary lumen under a very low applied pressure (e.g., 50 psi). Upon reduction of the temperature to below the VPT, the entangled state of the polymer coils in solution is restored as they re-dissolve in aqueous solution, providing effective DNA sequencing performance. An additional advantage of the thermo-responsive nanogels described in the present invention is that they can be designed to allow microchannel loading at room temperature, and then heated to the sequencing temperature for gel purposes. A number of thermo thickening polymer matrices have been developed based on polymers that exhibit thermo-associative behavior, with novel copolymer architectures such as poly-N-isopropylacrylamide-graft-polyethylene oxide (pNIPA-g-pEO) (see, e.g., Liang, D., et al., 1999 Macromolecules 32: 6326-63332; herein incorporated by reference in its entirety), poly-N-isopropylacrylamide-graftpolyacrylamide (pNIPA-g-LPA) (see, e.g., Sudor, J., et al., 2001 Electrophoresis 22: 720-728; herein incorporated by reference in its entirety), and pEO-polypropylene oxide block copolymers (pEO-pPO-pEO) (see, e.g., Liu, T., et al., 2001 Electrophoresis 22: 449-458; herein incorporated by reference in its entirety). These polymers utilize the self-associating properties of the hydrophobic chain parts, which serve as physical crosslinking points to form extended polymer networks when heated above the transition temperature.

EXAMPLES

Example 1

Reagents

Tris(hydroxymethyl)aminomethane (Tris), ethylenediaminetetraacetic acid (EDTA), ultrapure grade N,N,N',N'-tetraethylmethylenediamine (TEMED), ultrapure acrylamide, methylene bisacrylamide (Bis), and ammonium persulfate (APS) were purchased from Amresco (Solon, Ohio). N-[Tris(hydroxymethyl)methyl]-3-aminopropanesulfonic acid (TAPS) was obtained from Sigma (St. Louis, Mo.). Sorbitan monooleate (Span 80) was obtained from Fluka Chemical (St. Louis, Mo.). Isopar M (a C12-C14 isoparaffinic mixture) was obtained from Exxon (Houston, Tex.). MegaBACE Sequencing Standards (Amersham Pharmacia Biotech, Piscataway, N.J.) consisting of M13 DNA sequencing reaction products, labeled with energy-transfer dye primers and purified by standard ethanol precipitation by the manufacturer, were used without further purification. Beckman LongRead matrix was provided by Amersham Pharmacia Biotech.

Example 2

Polymeric Nanogel Synthesis

Figure 2:
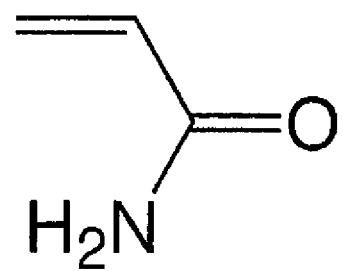
FIG. 2 shows structures of acrylamide (top) and N-methylene bisacrylamide (bottom).
Figure 2:
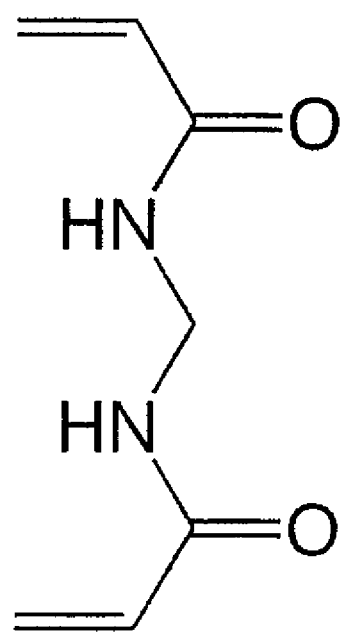

Structures of acrylamide and N-methylene bisacrylamide are shown in FIG. 2. Sparsely cross-linked nanogels were produced via inverse emulsion polymerization according to a protocol described in a previous report (see, e.g., Doherty, E. A. S., et al. 2003 Electrophoresis 24: 4170-4180; herein incorporated by reference in its entirety). The emulsion was formed as follows: A mixture of 40.53 g of Isopar M and 2.47 g of Span 80 was mixed briefly before being poured into the reaction vessel, a 500-mL water-jacketed reaction flask with a four-neck top (Kontes, Vineland, N.J.). The organic phase was immediately mixed by a high-torque overhead stirrer (Caframo Limited, Wiarton, Ontario, Canada) equipped with a homemade stainless steel shaft and a four-blade pitched-blade impeller, set at 600 rpm. The organic phase was degassed for 30 min using prepurified nitrogen (Air Products, Naperville, Ill.) that was further purified using an in-line oxygen/water vapor trap (Supelco, St. Louis, Mo.). A mixture of 22.8 g of acrylamide and 34.2 g of water was then added dropwise to the organic phase, resulting in a white, opaque emulsion. If sparsely cross-linked nanogels were desired, ~1 mL of an aqueous solution having the appropriate concentration of bifunctional monomer (Bis) was added immediately following the addition of the monomer solution. In the sparsely cross-linked nanogels of the present invention, Bis composed ~$10^{-4}$ mol % of the total number of moles of acrylamide monomer (see Table 1).

TABLE 1

Polymer Physical Properties

| polymer | mol % Bis ($\times 10^5$) | Mw ($\times 10^{-6}$ g/mol) | Rg (nm) | c* (mg/mL) |
| --- | --- | --- | --- | --- |
| LPA | 0.00 | 8.435 ± 0.759 | 331 ± 12 | 1.21 |
| LPA-LMM | 0.00 | 0.34 | 51 | n/a |
| LPA-HMM | 0.00 | 13.85 ± 1.88 | 251 ± 10 | 1.03 |
| LPA-UHMM | 0.00 | 20.56 ± 4.63 | 343 ± 27 | 0.71 |

TABLE 1-continued

Polymer Physical Properties

| polymer | mol % Bis ($\times 10^5$) | $M_w$ ($\times 10^{-6}$ g/mol) | $R_g$ (nm) | c* (mg/mL) |
|---|---|---|---|---|
| Nanogel-2x | 15.72 | 10.17 ± 1.43 | 230 ± 16 | 0.80 |
| Nanogel-4x | 31.44 | 11.45 ± 1.82 | 220 ± 18 | 0.89 |
| Nanogel-5x | 39.30 | 10.20 ± 1.15 | 236 ± 10 | 0.81 |
| Nanogel-6x | 45.16 | n/a[a] | n/a | n/a |

[a]Nanogel-6x matrix did not completely dissolve; MALLS and rheometry did not yield useful physical property data The resulting emulsion was then degassed for 1 h or until the emulsion temperature (measured and recorded using a Jenco Electronics (Lazar Research Laboratory, Los Angeles, Calif. thermocouple and data logger) exceeded 35° C., whichever was longer. Prior to initiation, a small aliquot of the emulsion was checked to ensure no autopolymerization had occurred. Polymerization was initiated with APS/TEMED, both at a concentration of 0.005 wt % (based on the mass of the aqueous phase). The reaction was allowed to proceed for 16 h under continuous mixing and degassing. The final product was precipitated by adding the product emulsion dropwise to a large volume of methanol with stirring. The precipitated polymer was washed copiously with methanol during filtration; product was dried in a room-temperature vacuum oven for at least 72 h.

The commercially available LPA matrix (provided by Amersham Pharmacia Biotech) was recovered from the prepackaged sequencing matrices by diluting the sequencing matrix in deionized, distilled water, then pouring the resulting diluted mixture into 1,000 Da molecular weight cutoff (MWCO) cellulose ester membranes (Spectrum Laboratories, Inc., Rancho Dominguez, Calif.). Diluted sequencing matrices were dialyzed against deionized, distilled water for 10 days with frequent water changes. The polymer solution was then frozen and lyophilized using a freeze-dry system (Labconco, Kansas City, Mo.), resulting in a white, stiff, foam-like mass. Polymer was redissolved in a solvent or buffer of interest by slow rotation for at least 24 hours (Roto-Torque, Cole-Parmer Instrument Company, Inc., Vernon Hills, Ill.).

Example 3

Multi-Angle Light Scattering (MALLS) for Nanogel and Linear Polymer Characterization Weight-average molar mass and radius of gyration of high molar mass polymer samples was determined by batch MALLS using a DAWN DSP Laser Photometer-Optilab DSP Interferometric Refractometer system (both, Wyatt Technology, Santa Barbara, Calif., USA) (see, e.g., Albarghouthi, M. N., et al. Electrophoresis 2002, 23 (10), 1429-1440; herein incorporated by reference in its entirety). Stock solutions of each polymer sample were prepared at concentrations of $1\times10^{-6}$ to $1\times10^{-4}$ g/mL (accurately determined to three significant figures) in 18.0-M$\Omega$ purified water from a Barnstead E-Pure system (Fisher Scientific, Glenlake, Ill., USA), where the deionized water used to dissolve the polymers was first passed through 0.02-µm filters (Whatman, Maidstone, England) to remove particulates. Polymer stock solutions were mixed by slow rotation on a Roto-Torque mixer (Cole-Parmer, Vernon Hills, Ill., USA) for at least 24 hours. Aliquots of the stock solution then were diluted with prefiltered solvent into precleaned scintillation vials (Fisher Scientific), and mixed using the Roto-Torque mixer. All dilutions were made using a high-precision balance to allow accurate calculation of concentration. A syringe pump (kdScientific, New Hope, Pa., USA) was used to push the samples through 0.8-µm syringe prefilters into the DAWN—Optilab system. For each dilution, the instrument was used to measure the refractive index (relative to the solvent) as well as the intensity of the scattered light as a function of angle for 16 different fixed angles.

Typically, 6-10 different polymer concentrations were analyzed for each Zimm plot. Pure solvent was the first and last injection to set the baseline for analysis. After the data are collected, the known concentrations were assigned to each plateau region, and Wyatt Technology ASTRA software was used to process the data and to create a Zimm plot. A subset of the 16 angles was chosen for data fitting to minimize the effect of noise, with data from no fewer than 8 angles utilized for the final results.

Figure 3A:
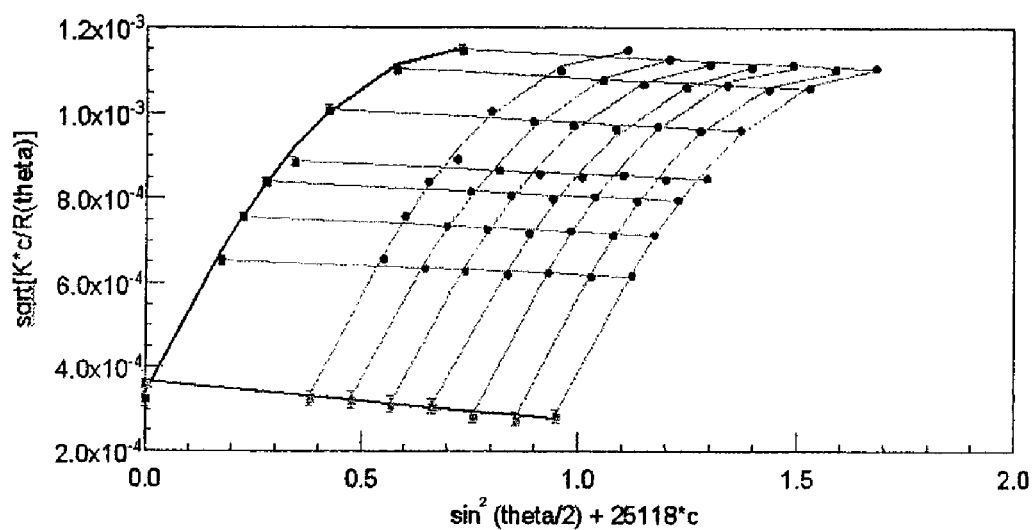
FIG. 3 shows Zimm plots (Berry formalism, with a first-order angle fit and a second-order concentration fit) for the commercially available LPA (bottom) and sparsely crosslinked nanogels (top).
Figure 3B:
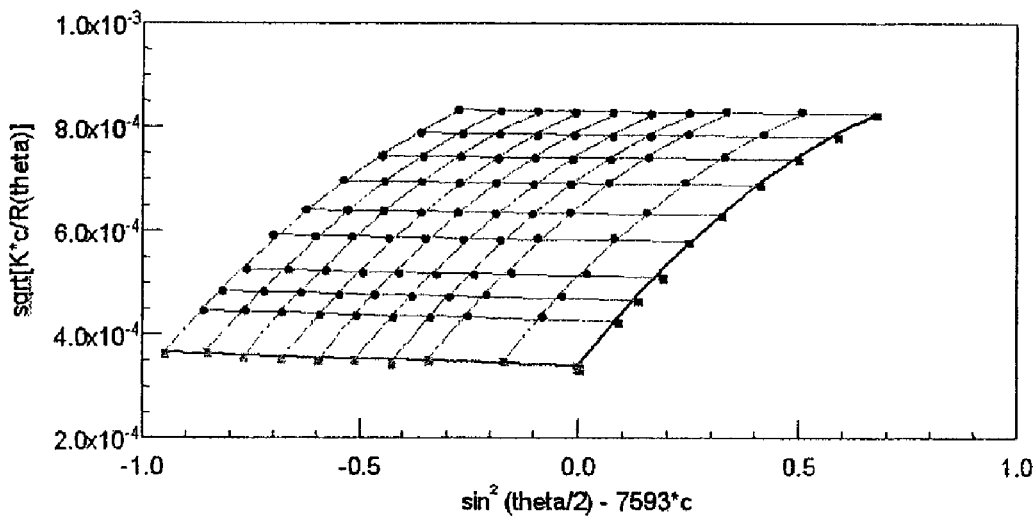

Batch multi-angle laser light scattering (MALLS) allows for the characterization of the weight average molar mass ($M_w$) and the z-average radius of gyration ($R_g$) of polymers that are too large to be fractionated via gel permeation chromatography (GPC) (see, e.g., Buchholz, B. A., Barron, A. E., Electrophoresis 2001, 22, 4118-4128; herein incorporated by reference in its entirety). Unlike GPC and tandem GPC-MALLS, batch MALLS is unable to provide the molar mass distribution of a polymer sample. Zimm plots (see, e.g., Wyatt, P. J., Analytica Chimica Acta 1993, 272, 1-40; herein incorporated by reference in its entirety) for the commercially available polymer (LPA) and two batches of sparsely crosslinked nanogels (Nanogel-1 and Nanogel-2) are shown in FIG. 3. The commercially available LPA has an $M_w$ of $8.909\pm0.209\times10^6$ g/mol and an $R_g$ of $167.8\pm2.8$ nm. The nanogels denoted Nanogel-1 have an $M_v$ of $8.495\pm0.836\times10^6$ g/mol and an $R_g$ of $235.4\pm10.2$ nm; nanogels denoted Nanogel-2 have an $M_w$ of $8.793\pm0.588\times10^6$ g/mol and an $R_g$ of $225.6\pm6.5$ nm. The present invention is not limited to a particular mechanism. Indeed, an understanding of the mechanism is not necessary to practice the present invention. Nonetheless, although all three polymers have a similar weight average molar mass, the sparsely crosslinked nanogels have a significantly larger z-average radius of gyration, which indicates the presence of a bimodal distribution of molar masses.

Example 4

Rheological Characterization of the Novel Polymeric Materials

Rheometry was performed using an Anton Paar Physica (Glen Allen, Va.) MCR 300 equipped with a Julabo USA, Inc. (Allentown, Pa.) digitally controlled recirculating water bath. Steady-shear rheometry was performed with a double-gap Couette fixture (model DG26.7) at 288 s$^{-1}$. Shear-dependent rheometry was performed with a 50-mm, 2° cone and plate fixture (model CP50-2) over a range of 0.1-100 s$^{-1}$. Data collection was accomplished using the US200 software provided by the rheometer manufacturer.

The overlap concentration (c*), or the concentration of polymer in solution at which polymer chains interact with each other in solution, is a critical measure of the extent of physical entanglements within a polymer solution, which in turn is critical to the DNA sequencing performance of a matrix. It has been shown that the ratio of polymer concentration to polymer overlap concentration (c/c*) can be used to "match" different, highly entangled linear polymer solutions used as DNA sequencing matrices (see, e.g., Heller, C., et al.

Electrophoresis 1999, 20, 1962-1977; Cottet, H., et al. Electrophoresis 1998, 19, 2151-2162; Viovy, J.-L., Duke, T., Electrophoresis 1993, 14, 322-329; each herein incorporated by reference in their entireties). This then allows the performance of these matrices to be compared on a fair basis. The extent of polymer-polymer entanglements control the lifetime of the virtual polymer "tube" that the DNA migrates through while under the influence of the electric field. Although scaling laws governing the pore size of the network differ with the exact chemical structure of the polymer (linear vs. crosslinked), the use of the c/c* matching to match pore size when comparing an entangled linear polymer network to an entangled polymer network containing very sparse crosslinks provides an accurate comparison of the two networks. Overlap concentrations for both LPA and nanogels (e.g., as experimentally determined by steady-shear rheometry (see, e.g., Barron, A. E., et al., J. Chromatogr. 1993, 652, 3-16; herein incorporated by reference in its entirety)) are shown in Table 2. The LPA has a higher overlap concentration, consistent with its smaller average $R_g$ as determined by light scattering.

TABLE 2

Polymer physical properties.

| Polymer | mol % Bis (×10$^5$) | $M_w$ (×10$^{-6}$ g/mol) | $R_g$ (nm) | c* (mg/mL) |
|---|---|---|---|---|
| LPA | 0.00 | 8.909 ± 0.209 | 168 ± 3 | 1.66 |
| Nanogels | 7.86 | 8.495 ± 0.836 | 235 ± 10 | 1.17 |

Figure 4:
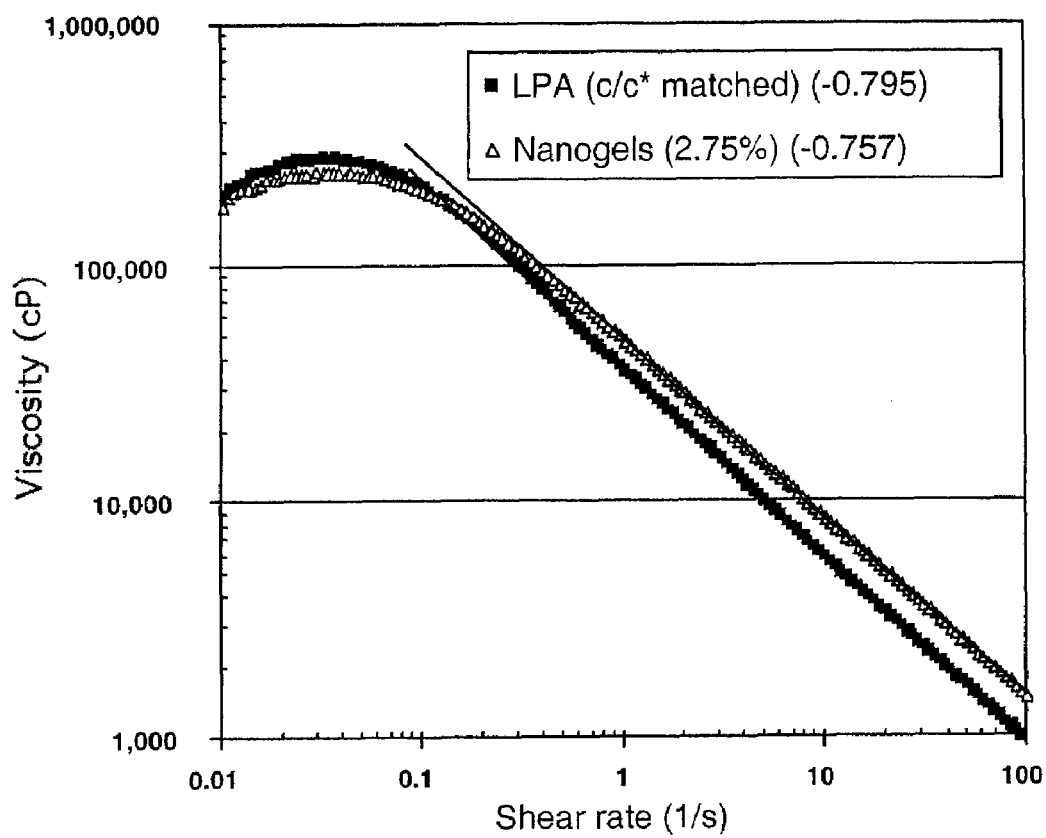
FIG. 4 shows flow curves of LPA and nanogel DNA sequencing matrices (all dissolved in 1×TTE, 7M urea) at 20° C. LPA matrices (open points) shear-thin to a greater extent than nanogel matrices (filled points). However, both show strong shear-thinning behavior. Power-law exponents of the best-fit through the shear-thinning region are listed in the legend.

Loading of sequencing matrices composed of linear polymers into microchannels is complicated, due to the high zero-shear viscosity of the matrix. Such difficulties are mitigated, for example, by the shear-thinning properties of the matrix (see, e.g., Goetzinger, W., et al. Electrophoresis 1998, 19, 242-248; herein incorporated by reference in its entirety). Matrix viscosity as a function of shear rate for the sequencing matrices employed in this work is shown in FIG. 4. The present invention is not limited to a particular mechanism. Indeed, an understanding of the mechanism is not necessary to practice the present invention. Nonetheless, as the shear rate applied to the highly entangled solution increased, polymer chains aligned with the flow, and the viscosity of the solution dropped with a power-law dependence of viscosity on shear rate, allowing highly concentrated polymer solutions to flow into microchannels. The power-law exponents listed in the legend of FIG. 4 indicate the extent of shear thinning. Even with sparse crosslinking, the nanogel matrix demonstrated significant shear-thinning and flows well under the applied pressures available in commercial sequencing instruments for loading of capillary arrays (e.g., ~1000 psi).

Use of a very small molar percentage of the difunctional monomer N,N-methylene bisacrylamide (Bis) as a comonomer for acrylamide produces the chemically crosslinked nanogel structure that stabilizes the final DNA sequencing matrix. To verify the incorporation of the crosslinker, as well as the relative percentage of Bis in the polymer nanogels, shear-rate dependent viscosity data were collected for three nanogel batches having varying crosslink densities. Nanogels having similar overlap concentrations were used at the same concentration, in order to more accurately compare the power-law regions of the shear-dependent viscosity data. The magnitude of the power law exponent of the shear-thinning region of each flow curve decreased as the chemical crosslink density increased. The present invention is not limited to a particular mechanism. Indeed, an understanding of the mechanism is not necessary to practice the present invention. Nonetheless, these results indicate that the amount of crosslinker incorporated into the nanogels is proportional to the amount that is included in the comonomer polymerization reaction mixture.

Example 5

DNA Sequencing Using Nanogel-Based Separation Matrices

DNA sequencing was performed on a MegaBACE 1000™ CAE instrument (Molecular Dynamics, Sunnyvale, Calif.) equipped with 6×16 fused-silica capillary arrays (75 μm inner diameter, 64-cm total length, 40-cm effective length) covalently coated with LPA. MegaBACE™ Sequencing Standards (Amersham Pharmacia Biotech, Piscataway, N.J.) consisting of M13 DNA sequencing reaction products, labeled with energy transfer dye primers and purified by standard ethanol precipitation by the manufacturer, were used without further purification.

Polymers to be tested as DNA sequencing matrices were dissolved at the concentration of interest in a 1×TTE (50 mM Tris (Amresco, Solon, Ohio), 50 mM TAPS (Sigma, St. Louis, Mo.), 2 mM EDTA (Amresco, Solon, Ohio)) buffer. Sequencing matrices were loaded under a pressure of 1000 psi, followed by a relaxation time of 20 minutes and a prerun electrophoresis for 5 minutes at 140 V/cm. After electrokinetic sample injection at 93.75 V/cm for 40 seconds, separation of DNA was performed at 140 V/cm and 44° C. for 120 minutes. Laser-induced fluorescence (LIF) data were collected, analyzed, and translated into called DNA sequence using the MegaBACE 1000 DNA Sequencing Software Version 2.0™.

Raw LIF data were extracted from the MegaBACE sequencing software and fitted into Gaussian peaks using PeakFit™ 4.06 (SPSS, Chicago, Ill.) from which the full width at half-maximum (FWHM) and the migration time was calculated for each peak. An equation for migration time as a function of base number was determined by fitting the data provided by PeakFit to a third-order polynomial function, a trend observed within high-molar mass LPA matrix by Karger and co-workers (see, e.g., Carrilho, E., et al. Anal. Chem. 1996, 68 (19), 3305-3313; herein incorporated by reference in its entirety). This equation was used to calculate the selectivity of the sequencing matrix as $$S_n = 2(\mu_n - \mu_{n-1})/(\mu_n + \mu_{n-1}) \quad (1)$$

where $\mu_n$ is the apparent mobility of the n-th DNA fragment and $\mu_{n-1}$ is the apparent mobility of the (n–1)-th DNA fragment. Peak width (FWHM) as a function of base number was plotted and fit to a second-order polynomial. This function best modeled the experimental data; a similar empirical fitting function has been successfully employed to characterize other sequencing matrices (see, e.g., Madabhushi, R. S., et al. Electrophoresis 1998, 19, 224-230; Menchen, S., et al., Electrophoresis 1996, 17 (9), 1451-1459; each herein incorporated by reference in their entireties).

Figure 5A:
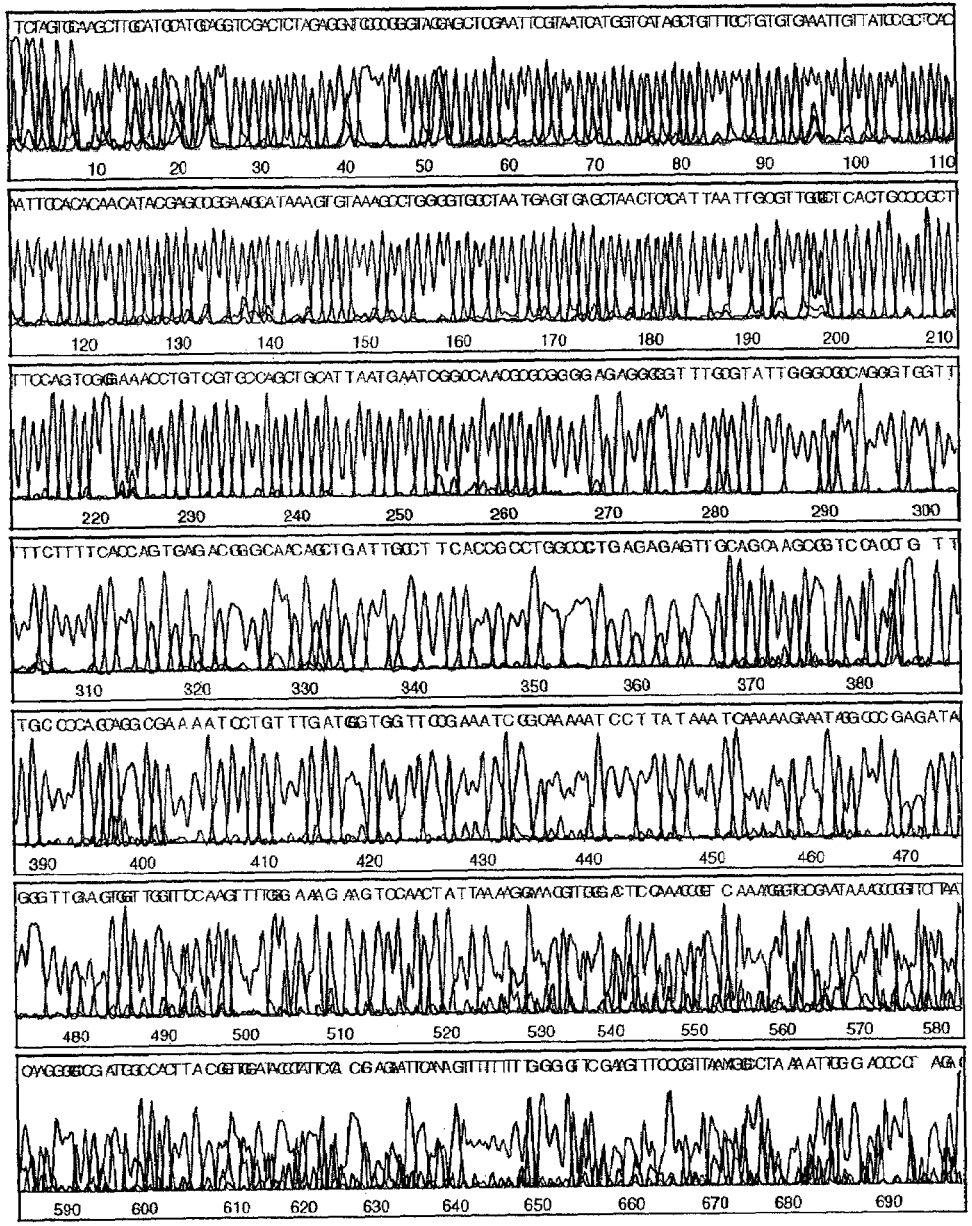
FIG. 5 shows a) Electropherogram representing the average performance of the LPA (c/c* matched) matrix. b) Electropherogram representing the average performance of the nanogel matrix. Electrophoresis conditions are as described herein below.
Figure 5B:
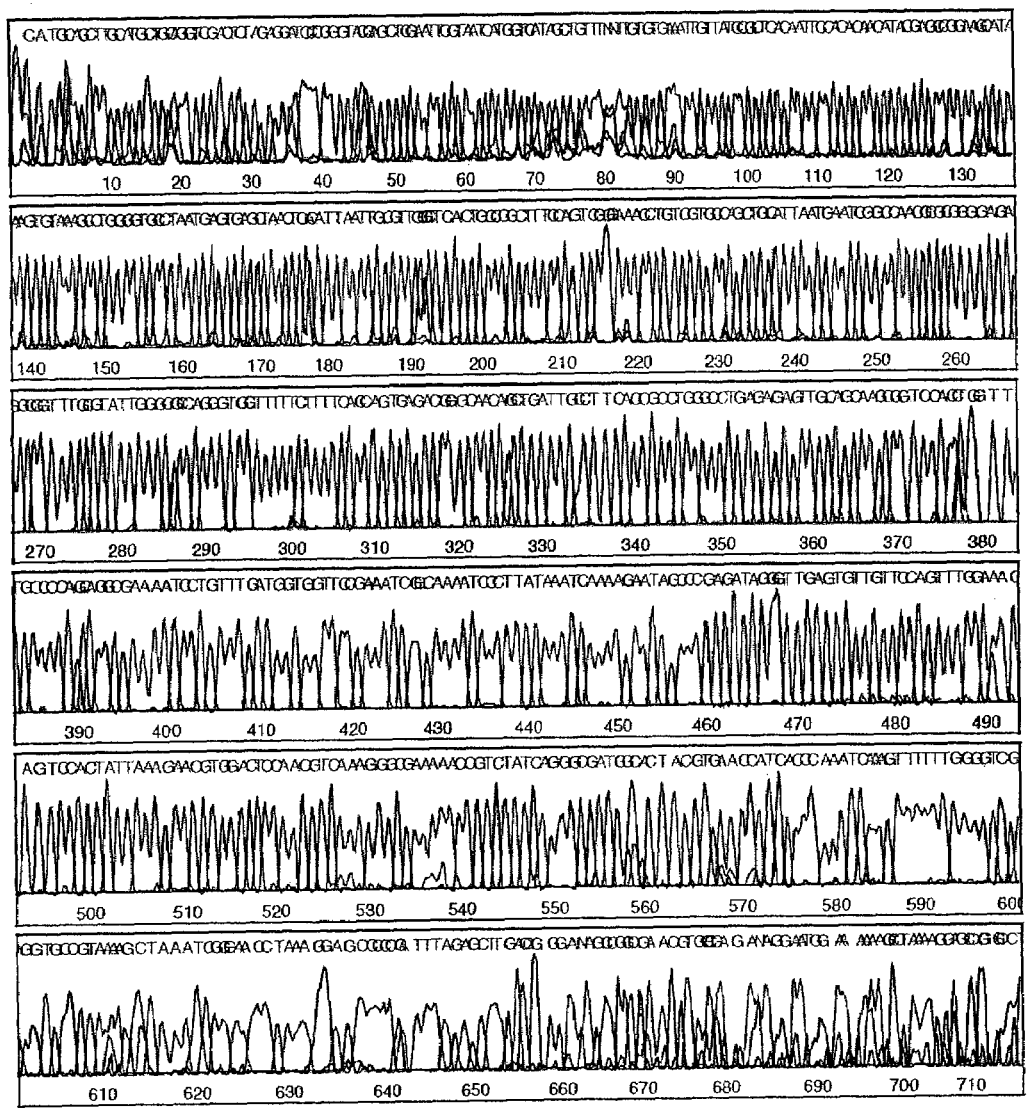

Table 3 lists the read lengths obtained at 98.5% base-calling accuracy for linear polyacrylamide and sparsely crosslinked polyacrylamide nanogel matrices. When the LPA concentration is c/c* matched with the concentration of nanogels, the matrix composed of nanogels provides a 10.4% extension of read length at 98.5% base-calling accuracy and a significantly more reproducible performance (666±10 bases for nanogels vs. 603±26 bases for LPA; representative electropherograms are shown in FIG. 5).

TABLE 3

DNA sequencing read lengths (120 minute run).

| | | 98.5% accuracy | |
|---|---|---|---|
| Polymer sample | Conc. (w/v %) | Read length* | % improvement |
| LPA† | 3.87 | 603 ± 26 | — |
| Nanogel† | 2.75 | 666 ± 10 | 10.4 |

†matched for c/c*
*error indicates the standard deviation in the data (n = 7)

Note that, while the present examples are directed to base calling using sequences of about 600 base pairs in length, those of skill in the art will be able to obtain ultra-long reads using commercial base-calling software, standard DNA samples with no subsequent purification, and performing sequencing at 44° C. (see, e.g., He, H., et al., Electrophoresis 2002, 23 (10), 1421-1428; herein incorporated by reference in its entirety). Further, those of skill in the art may produce blended matrices, which could serve to increase the resolution of short DNA fragments (see, e.g., Carrilho, E., et al. Anal. Chem. 1996, 68 (19), 3305-3313; Zhou, H., et al. Anal. Chem. 2000, 72 (5), 1045-1052; each herein incorporated by reference in their entireties). The separation time for all separations was 120 minutes. The present invention is not limited to a particular mechanism. Indeed, an understanding of the mechanism is not necessary to practice the present invention. Nonetheless, it is contemplated that DNA migration is not appreciably slowed due to the presence of the sparse chemical crosslinks.

DNA-polymer and polymer-polymer interactions dictate DNA separation mechanisms. For large ssDNA that migrates via reptation within the polymer matrix, network rupture, or dragging of polymer chains by migrating DNA, can destroy resolving power by temporarily changing the network structure of the entangled matrix (see, e.g., Albarghouthi, M. N., et al. Electrophoresis 2001, 22, 737-747; herein incorporated by reference in its entirety).

Figure 6A:
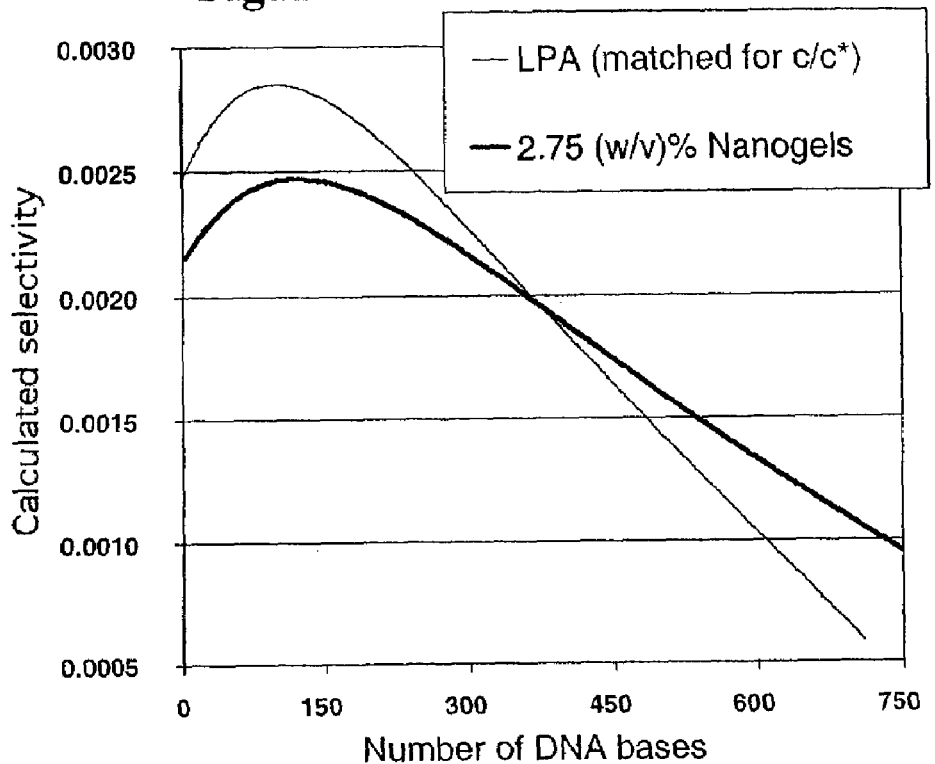
FIG. 6 shows selectivity (top) and peak width (bottom) as a function of DNA base number for LPA and nanogel DNA sequencing matrices.
Figure 6B:
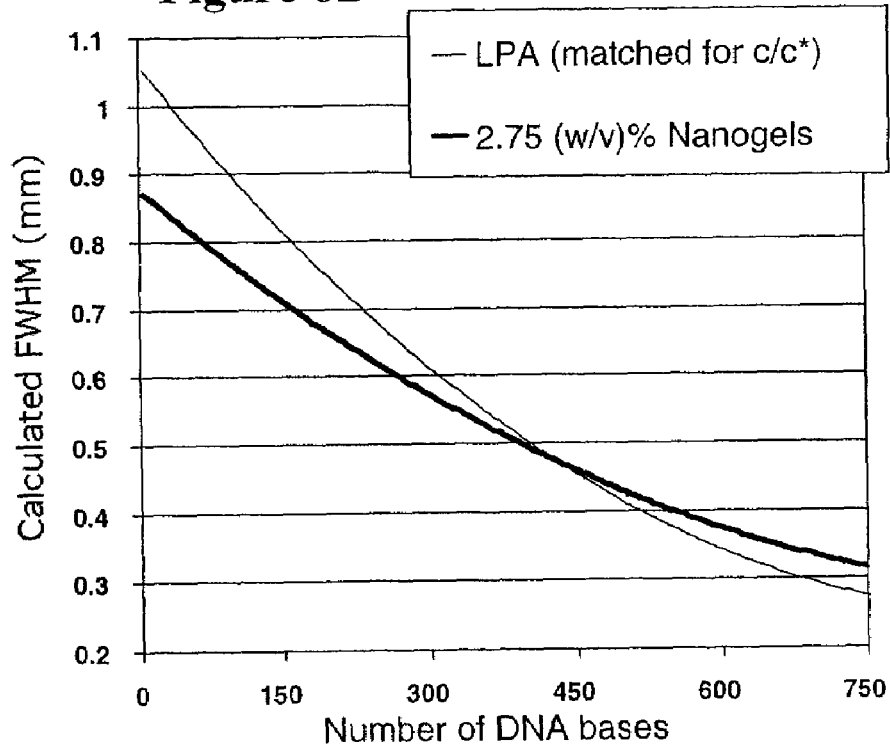

The present invention is not limited to a particular mechanism. Indeed, an understanding of the mechanism is not necessary to practice the present invention. Nonetheless, it is contemplated that chemical crosslinks make the matrix more stable to matrix disruption caused by DNA motion, possibly explaining the longer read lengths. It is also contemplated that the improved sequencing performance of the nanogel matrix is due to improved selectivity, decreased peak widths, or a combination of both factors. In order to extend DNA sequencing read lengths, the selectivity, or peak spacing, of long ssDNA separation should be increased, or the peak widths of the long ssDNA fragments should be decreased. The selectivity and peak width as a function of base number provided by LPA and nanogel sequencing matrices are shown in FIG. 6.

DNA sequencing matrices composed of nanogels of the invention provide higher-selectivity separations than the LPA matrices for large sequencing fragments. Not surprisingly, lower selectivity is observed for ssDNA shorter than 375 bases, due to the lower overall concentration of the nanogels (see, e.g., Salas-Solano, O., et al. Anal. Chem. 1998, 70 (19), 3996-4003; herein incorporated by reference in its entirety). However, this does not compromise base-calling for shorter fragments (they are still well-separated). In particular, a 2.75 (w/v) % nanogel matrix provides improved selectivity for ssDNA longer than 375 bases when compared to the LPA matrix that was matched for c/c*.

The improvement in selectivity of large sequencing fragments provided by nanogel sequencing matrices is somewhat offset by ssDNA peak widths that are similar to or wider than those seen in LPA matrices for sequencing fragments longer than approximately 450 bases. This is unexpected, since chemical crosslinks are thought to reduce diffusion within microchannel in situ polymerized crosslinked gels (see, e.g., Ugaz, V. M., et al. Electrophoresis 2002, 23 (16), 2777-2787; herein incorporated by reference in its entirety).

The present invention is not limited to a particular mechanism. Indeed, an understanding of the mechanism is not necessary to practice the present invention. Nonetheless, it is possible that the comparison of an entangled linear polymer network with an entangled network of polymer containing sparse crosslinks solely on the basis of the extent of entanglements (c/c*), which led to a moderate disparity in polymer concentration between the two matrices, may have a slight effect on the pore size. This could explain the similar or wider ssDNA peak widths. It is also possible that a higher nanogel crosslink density may, for example, be needed to impact ssDNA peak widths for large DNA. Indeed, it was found that when the percentage of cross-linker was increased from $7.9 \times 10^{-6}$ mol % to $3.9 \times 10^{-4}$ mol %, narrower peak widths were obtained for large DNA sequence fragments, which contributed to the obtainment of longer DNA sequencing read lengths. Finally, it is also contemplated that an appropriate blend of linear polymer and nanogels may, for example, improve the DNA sequencing read length by further improvements in selectivity or sample peak width, both for small and large DNA. In addition, the other nanogel batches produced under identical conditions also out-performed the matched LPA matrix.

It is noted that if thermoresponsive monomers (e.g., N,N-diethylacrylamide or methyoxyethyl acrylamide) are used for the formation of these sparsely cross-linked nanogels, then temperature-induced volume phase transitions could be exploited to facilitate easier microchannel loading procedures under moderate applied pressures (see, e.g., Buchholz, B. A., et al., 1999 Electrophoresis 20: 1962-1977; herein incorporated by reference in its entirety).

Example 6

Fabrication and Design of a Microfluidic Device for DNA Separation

The microfabrication procedure and chip design are described in previous reports (see, e.g., Simpson, P. et al., 1998 PNAS 95: 2256-2261; Paegel, B. M., et al., 2002 PNAS 99: 574-579; each herein incorporated by reference in their entireties). Briefly, Borofloat glass wafers (150-mm diameter; Schott, Yonkers, N.Y.) coated with a 2000-Å amorphous silicon film and spin-coated with photoresist (S1818, Shipley, Marlborough, Mass.) were used. The channel pattern was exposed and developed using standard photolithography processes and then transferred to the silicon film by reactive ion etching with SF6 plasma to expose the glass layer. The wafer was then isotropically etched in concentrated HF for 3.5 min to create channels with a depth of 25 μm. Reservoirs were diamond-drilled using a CNC mill, and after cleaning, this glass wafer was thermally bonded to a blank glass substrate at 670° C. to form a closed-channel sandwich structure. The 96 separation channels were arrayed around a common central anode. Adjacent pairs of lanes are grouped to share cathode and waste reservoirs. The widths of the separation channels are 200 μm after etching and the effective separation length is 15.9 cm.

Example 7

Operation of a Microfluidic Device for DNA Sequencing

The microchannels were precoated with LPA according to a modified Hjerten procedure (see, e.g., Hjerten, S. J. 1985 J. Chromatogr. 347: 191-198; herein incorporated by reference in its entirety). Before matrix loading, the separation channels and reservoirs at the cathode end of the array are filled with deionized water. The linear polyacrylamide sieving matrix is then forced in through the anode access port at 300 psi for 3 min by using a high-pressure loading system (see, e.g., Scherer, J. R. et al., 2001 Biotechniques 31: 1150; herein incorporated by reference in its entirety). Excess matrix is removed from the sample wells and 1.8 µL of sample introduced. The cathode and waste buffer moats are filled with 3 mL of 5×TTE each. An elastomer buffer reservoir is affixed above the central anode access port and filled with 3 mL of 5×TTE. The filled PCAE device is placed on a stage heated to 67° C. on the four-color confocal rotary scanner. An electrode ring array is placed over the chip to provide electrophoresis voltages to the various reservoirs. A PDMS ring was applied to the chip to create a continuous buffer reservoir to electrically address the cathode and waste reservoirs simultaneously. The sample is injected electrokinetically from the sample reservoir to the injection intersection at 190 V/cm for 35 s. During this period, the anode and cathode reservoirs are floated. The plug defined by the 250-µm intersection is driven down the separation column at 150 V/cm while a back-biasing electric field of 200 V/cm is applied at the sample and waste reservoirs to withdraw excess sample and prevent leakage from the reservoirs onto the column during the separation. Electrophoretic analysis is complete in 24 min.

Example 8

Data Acquisition and Reduction

The scanning system involves a four-color rotary scanner (see, e.g., Shi, Y. N., et al., 1999 Anal. Chem. 71: 5354-5361; herein incorporated by reference in its entirety). Briefly, excitation at 488 nm from an argon ion laser is coupled into the optical path with a dichroic beam splitter. The laser light is passed through the hollow shaft of a stepper motor, displaced from the rotation axis by 1 cm with a rhomb prism, and focused on the microchannels through a 60× objective. Fluorescence is collected by the objective and passed back through the hollow shaft and dichroic beam splitter and sorted into four spectral channels. Data acquisition procedures have been described elsewhere (see, e.g., Paegel, B. M. et al., 2002 PNAS 99: 574-579; herein incorporated by reference in its entirety). After electrophoretic analysis, the four-color electropherograms were used as input for the MegaBACE Sequence Analyzer.

Example 9

Sparsely Cross-Linked Nanogel Matrix Synthesis

Nanogels were synthesized via inverse emulsion polymerization, precipitated in methanol, washed, filtered, and dried, resulting in a free-flowing white powder that is easily handled. Resulting nanogels were dissolved in sequencing buffer in 48-72 hours by slow rotation and/or slow mechanical stirring. Nanogels had a molar mass of $10-12 \times 10^6$ g/mol and a z-average radius of gyration of 220-240 nm. These polymer structures were discrete and sparsely internally crosslinked, and were able to form highly entangled matrices for DNA sequencing. Although researchers have produced non-linear polyacrylamide-based structures for DNA separations, these relatively low molar mass (~$1 \times 10^6$ g/mol) copolymers were designed to combine the properties of their respective linear homopolymers and were not tested as DNA sequencing matrices.

The initial proof-of-principle results were obtained using nanogels with $7.86 \times 10^{-5}$ mol % Bis (Nanogel-1×). Assuming complete conversion of all monomer to a monodisperse polymer having a molar mass of $10 \times 10^6$ g/mol (see below) containing $8 \times 10^{-5}$ mol % Bis, approximately 15% of the initiated polymers in these previously studied materials contain one or more Bis crosslinks at the 1× crosslink density. Optimization of these structures with respect to crosslink density was investigated using nanogels with $6.29 \times 10^{-5}$ mol % Bis to $4.72 \times 10^{-4}$ mol % Bis (0.8× to 6×). ~75% of the polymer chains incorporate at least one point of crosslinking.

The average molar mass and z-average radius of gyration of the nanogels were measured using multi-angle laser-light scattering (MALLS) in batch mode (see, e.g., Buchholz, B. A., et al. Anal. Chem. 2001, 73, 157-164; herein incorporated by reference in its entirety). Overlap threshold concentrations, which correlate with the onset of polymer-polymer entanglement interactions, were determined using steady-shear rheometry to measure specific viscosity of the polymer solution as a function of concentration. Physical properties of the linear polymers and sparsely crosslinked polymer nanogels presented in this work are shown in Table 2.

Comparison of linear polymer matrices and matrices composed of sparsely crosslinked nanogels should be done on an equal basis (e.g., the properties of the linear polymer matrix and the sparsely crosslinked polymer matrix should be as similar as possible) notwithstanding the presence or absence of chemical crosslinks. It has been shown that the ratio of polymer concentration to polymer overlap concentration (c/c*) can be used to "match" different, highly entangled linear polymer solutions used as DNA sequencing matrices. This then allows the performance of these matrices to be compared on an equal basis. The extent of polymer-polymer entanglements control the lifetime of the virtual polymer "tube" that the DNA migrates through while under the influence of the electric field. The present invention is not limited to a particular mechanism. Indeed, an understanding of the mechanism is not necessary to practice the present invention. Nonetheless, although scaling laws governing the mesh size of the network differ with the exact chemical structure of the polymer (linear vs. crosslinked), the use of the c/c* matching to match mesh size when comparing an entangled linear polymer network to an entangled polymer network containing very sparse crosslinks should still provide an accurate comparison of the two networks. Matrices were matched according to the extent of interchain entanglements (c/c*) and according to average molar mass.

Preliminary work with nanogels having a crosslink density of ~$8 \times 10^{-5}$ mol % indicated that the presence of chemical crosslinks at that density improves sequencing read lengths by 10.4% compared to the appropriately matched LPA matrix. This improvement in read length was provided by the improved selectivity of ssDNA fragments longer than 350 bases in the nanogel sequencing matrix (see, e.g., Doherty, et al., 2003 Electrophoresis 24: 4170-4180; herein incorporated by reference in its entirety). Previous studies have shown that the optimization of nanogel crosslink density provides further improvement in sequencing performance compared with LPA (see Table 3). Sparsely crosslinked acrylamide matrices showed improvements in read length at 98.5% accuracy; in particular, the Nanogel-5× matrix provided the longest read lengths at 98.5% accuracy as well as an 18.7% improvement in read length over the c/c*-matched LPA matrix. Using CAE, a routine average read length of 674 bases could be obtained in the nanogel matrix; in the best case, high-accuracy read lengths as long as 726 bases were achieved. By comparison, the c/c*-matched LPA matrix gave 568-base reads at best.

Within a sequencing chip, the Nanogel-5× matrix provided excellent read lengths in under 30 minutes.

Above the 5× crosslink density, the nanogels did not fully dissolve in sequencing buffer, forming a cloudy, inhomogeneous polymer solution that was unable to provide routine read lengths over 600 bases at 98.5% accuracy for CAE.

High-molar mass LPA networks have been shown to provide read lengths much greater than 600 bases in a single run, when several parameters, including sample preparation, capillary wall coatings, matrix formulation (blends of low- and high-molar mass LPA), sequencing temperature, and base-calling algorithms, are completely optimized (see, e.g., Carrilho, E., et al. Anal. Chem. 1996, 68 (19), 3305-3313; Zhou, H., et al. Anal. Chem. 2000, 72 (5), 1045-1052; each herein incorporated by reference in their entireties).

Improvements in read length can stem from an increased selectivity of the matrix (increased peak spacing), decreased sample peak widths, or a combination of both factors. The Nanogel-5× matrix has a lower selectivity for small DNA (<250 bases), but commercial base-calling software is able to easily distinguish sample peaks at this selectivity. For large DNA (>600 bases) the selectivity of the three matrices is similar. Instead, the improvement provided by increasing the crosslink density (up to 5×) may be attributed to decreased peak widths provided by increasing the crosslink density.

Blends of high molar mass and low molar mass LPA have been employed by Karger and co-workers to improve DNA sequencing read lengths (see, e.g., Salas-Solano, O., et al. Anal. Chem. 1998, 70 (19), 3996-4003; Zhou, H., et al. Anal. Chem. 2000, 72 (5), 1045-1052; each herein incorporated by reference in their entireties). The use of low- and high-molar mass linear polymer within a nanogel matrix containing sparse crosslinks was expected to follow trends that are similar to those seen in linear polymer blends. In particular, low molar mass polymer should improve the resolution of small DNA fragments by creating a range of smaller mesh sizes for the separation of small ssDNA. High molar mass polymer should provide a more stable entangled network for the improved separation of large ssDNA fragments. The Nanogel-5×DNA sequencing matrix showed the most promising DNA sequencing performance. Using this matrix as a starting point, four blends, each primarily composed of nanogels and having a total polymer concentration of 2.75 (w/v) %, were formulated and tested (see Table 5).

Blend 1 was designed to improve the selectivity of the matrix for small ssDNA separation due to the presence of a distribution of smaller mesh sizes within the sequencing matrix, and would be expected to have the lowest overall viscosity because of the inclusion of low molar mass LPA. Blend 2 should improve the selectivity of the matrix for large sequencing fragments. Blend 2 was more robust than Blend 1 considering the inclusion of 0.25% high-molar mass LPA (e.g., $M_w \sim 14 \times 10^6$ g/mol). Blend 3 was designed to have some combination of the characteristics of Blends 1 and 2. Blend 4, which includes 0.25% of an ultra-high molar mass LPA ($M_w \sim 21 \times 10^6$ g/mol) along with 2.50% nanogels, was designed to have the greatest network stability and should give good separation of large DNA fragments.

Table 5 shows the read lengths at 98.5% accuracy provided by the four blends. The addition of a low percentage of low molar mass polymer to the nanogels (Blend 1) improved the matrix selectivity for short ssDNA as expected. The addition of a small fraction of high molar mass linear polymer to the nanogels (Blend 2) decreased peak widths for large sequencing fragments. Blend 3, a mixture of nanogels, high molar mass polymer, and low molar mass polymer, gave intermediate performance as expected, showing improved resolution of most DNA sequencing fragments (up to ~550 bases), but the DNA peak widths in this matrix were wider than in the other two blends. Thus, it is contemplated that the replacement of 0.50 (w/v) % of sparsely crosslinked polymer with linear polymer led to broader DNA peak widths, by allowing increased DNA diffusion.

The present invention is not limited to a particular mechanism. Indeed, an understanding of the mechanism is not necessary to practice the present invention. Nonetheless, it may be that high-molar mass, sparsely crosslinked nanogels form networks that are essentially as stable as an ultrahigh-molar mass ($>20 \times 10^6$ g/mol) LPA network. Note that the average molar mass of the nanogels in this case is only ~$10 \times 10^6$ g/mol, hence the matrix viscosity is substantially lower than $20 \times 10^6$ g/mol LPA.

Using the Nanogel-5× matrix as a starting point, two LPA-nanogel blends having a total polymer concentration of 3.00 (w/v) % were formulated and tested as DNA sequencing matrices (see Table 6).

TABLE 4

DNA sequencing read lengths at 98.5% accuracy. LPA is c/c* matched for each nanogel crosslink density.

| Polymer | Concentration (w/v)% | Average read length[†] | Best read length | % improvement (average) |
|---|---|---|---|---|
| LPA | 4.47 | — | 512 | — |
| Nanogel-2× | 3.00 | 629 ± 28 (n = 14) | 673 | 22.9 |
| LPA | 3.70 | — | 626 | — |
| Nanogel-4× | 2.75 | 655 ± 25 (n = 14) | 685 | 4.6 |
| LPA | 4.05 | — | 568 | — |
| Nanogel-5× | 2.75 | 674 ± 32 (n = 14) | 726 | 18.7 |
| LPA | — | — | — | — |
| Nanogel-6× | 3.00 | 549 ± 55 (n = 9)[‡] | 618 | — |

[†]Error indicates the standard deviation in the data.
[‡]Nanogel-6× matrix did not completely dissolve, resulting in a cloudy, inhomogeneous solution that was unable to provide routine sequencing > 600 bases.

TABLE 5

DNA sequencing read lengths at 98.5% accuracy for LPA-nanogel blends (total polymer concentration 2.75 (w/v)%).

| | Blend Composition | Average read length[†] | Best read length |
|---|---|---|---|
| 1 | 2.50% Nanogel-5× + 0.25% LPA-LMM | 588 ± 74 (n = 13) | 677 |
| 2 | 2.50% Nanogel-5× + 0.25% LPA-HMM | 658 ± 28 (n = 14) | 697 |
| 3 | 2.25% Nanogel-5× + 0.25% LPA-LMM + 0.25% LPA-HMM | 635 ± 28 (n = 14) | 683 |
| 4 | 2.50% Nanogel-5× + 0.25% LPA-UHMM | 678 ± 20 (n = 10) | 717 |

[†]Error indicates the standard deviation in the data.

TABLE 6

DNA sequencing read lengths at 98.5% accuracy for LPA-nanogel blends (total polymer concentration 3.00 (w/v)%).

| Blend Composition | Average read length[†] | Best read length |
|---|---|---|
| 5  2.75% Nanogel-5x + 0.25% LPA-LMM | 683 ± 8 (n = 14) | 694 |
| 6  2.75% Nanogel-5x + 0.25% LPA-UHMM | 674 ± 10 (n = 14) | 691 |

[†]Error indicates the standard deviation in the data.

These blends performed similarly to the Nanogel-5x matrix, with Blend 5, a low-molar mass LPA-nanogel blend, showing slight improvement with an average read length of 683±8 bases (n=14) at 98.5% accuracy. Blends having a higher total polymer concentration provided highly reproducible read lengths (RSD <1.6%).

Highly crosslinked polymer networks, such as those developed in the early 1990s as in-situ polymerized capillary gels, were impractical for high-throughput sequencing due to the difficulty or impossibility of replacing the gel between sequencing runs. The novel use of sparse crosslinking in a highly entangled network of nanogels provides a shear-thinning polymer solution, which allows for the replacement of the matrix between runs within a commercial CAE instrument as well as in a chip-based sequencing instrument with a custom-built matrix loading device. Substitution of a small proportion of the Nanogel-5x matrix with low molar mass LPA (Blend 2) lowered the matrix viscosity; replacement of a small proportion of the Nanogel-5x matrix with very high molar mass LPA (Blend 4) increased the viscosity slightly. Both Blends 5 and 6, with a total polymer concentration of 3.00 (w/v) %, were more viscous than the Nanogel-5x matrix.

The present invention is not limited to a particular mechanism. Indeed, an understanding of the mechanism is not necessary to practice the present invention. Nonetheless, based on these results, the use of sparse crosslinking for entangled polymer network stabilization shows significant utility for DNA sequencing applications. The presence of sparse crosslinks improved the selectivity of the matrix for large ssDNA sequencing fragments and, at the optimized crosslink concentration, improved read lengths by reducing sample peak widths. This highly entangled network of acrylamide-based nanogels is the first material that outperforms highly entangled LPA as a sequencing matrix, when the linear and sparsely crosslinked polymers are matched for molar mass as well as the extent of interchain entanglements (c/c*). Polymer network stabilization through occasional chemical crosslinking may aid in the stabilization of other polymers used for DNA sequencing. In particular, this approach to polymer network stabilization improves the performance of thermo-thinning (see, e.g., Buchholz, B. A., et al. Anal. Chem. 2001, 73, 157-164; herein incorporated by reference in its entirety) or thermo-thickening polymer networks, which may be loaded in a low-viscosity state and subsequently used for DNA sequencing as robust, highly entangled matrices.

Example 10

Synthesis of Thermo-Responsive Nanogels

PolyDEA nanogels were synthesized at 70° C. via emulsion precipitation polymerization, following the approach used to create polyNIPA nanogels, which have a VPTT very close to that of polyDEA. In further experiments with 40 wt %/60 wt % of DEA/DMA feed ratio it was unexpectedly found that a mixed DEA and DMA monomer aqueous solution formed a macroscopic precipitate shortly after the initiation of polymerization at 70° C. This phenomenon was found to occur over a wide range of DEA/DMA feed ratios, ranging from 70%/30% (w/w) to 40%/60% (w/w). Alternate synthesis conditions were explored to address this issue. Experiments showed that the synthesis of DEA/DMA nanogels should be carried out within a narrow range of reaction temperature which depends on copolymer composition, above the initial phase transition temperature and below the critical precipitation temperature above which DEA/DMA copolymer particles form a macroscopic precipitate. The reaction temperature was varied, crosslinker density, monomer ratio, and reaction time to investigate the effect of synthesis conditions on the size and size distribution of the nanogels. The temperature-dependent phase transition behaviors of the resulting DEA-DMA nanogels, both in water and in aqueous NaCl solutions, were studied by dynamic light scattering and visible-light spectrophotometry.

Ultrapure (>99.5%) monomers of N,N-diethylacrylamide (DEA) and N,N-dimethylacrylamide (DMA) were purchased from Monomer-Polymer and Dajac Labs (Feasterville, Pa.) by custom order. The crosslinker methylene-bis-acrylamide (Bis), ammonium persulfate (APS), sodium dodecyl sulfate (SDS) and N,N,N',N'-tetramethylethylenediamine (TEMED) were from Amresco (Solon, Ohio). Deionized water was used throughout.

PolyDEA nanogels were synthesized via emulsion precipitation polymerization. In a typical synthesis, 2.4 g DEA monomer, 0.08 g SDS surfactant and 0.24 g Bis were dissolved in 187.6 g water. The solution was stirred under nitrogen. After the solution was brought to 70° C. under nitrogen, 10 ml of a 0.01 g/ml aqueous APS solution was added to initiate polymerization. The polymerization was carried out at 70° C. for 4 hrs under nitrogen. The resultant polyDEA nanogels were dialyzed through a cellulose membrane (Carolina Biological Supply Company, N.C.) for 10 days to remove unreacted monomers, small molecules and the SDS surfactant.

The DEA/DMA nanogels were synthesized via surfactant-free emulsion precipitation polymerization. DEA/DMA nanogels were prepared from 2.86 g of DEA and DMA monomer with four different DEA/DMA compositions (70%/30%, 60%/40%, 50%/50%, 40%/60%, w/w), 0.286 g Bis (10 wt % of total feed amount of DEA and DMA), and 0.1 g APS. The DEA and DMA monomers and BIS crosslinker were dissolved in 187.7 g water. Following the addition of APS, the polymerization was carried out, at different reaction temperatures for the four different compositions. These copolymer nanogels were dialyzed (Carolina Biological Supply Company, N.C.) for 10 days to remove unreacted monomers and small molecules. The dialyzed nanogels were freeze-dried for further re-dispersion. The specific synthesis conditions used were given in Table 7.

TABLE 7

Synthesis conditions and properties of DEA/DMA nanogels

| DEA/DMA nominal feed ratio | DEA/DMA real ratio from $^1$H NMR | Reaction T (° C.) | Reaction t (hour) | BIS (wt %) | APS (g) | TEMED (g) | <D> (nm) | PDI | $M_w$ (×10$^7$) (g/mol) |
|---|---|---|---|---|---|---|---|---|---|
| 100%/0 | 100%/0 | 70 | 4 | 10 | 0.1 | 0 | 298 | 0.18 | 19.2 |
| 70%/30% | 71.4%/28.6% | 37 | 4 | 10 | 0.1 | 0.05 | 232 | 0.44 | 3.24 |
| 60%/40% | 60.9%/39.1% | 46 | 4 | 10 | 0.1 | 0.05 | 214 | 0.45 | 2.65 |
| 50%/50% | 52.1%/47.9% | 54 | 4 | 10 | 0.1 | 0 | 252 | 0.48 | 3.89 |
| 40%/60% | 40.9%/59.1% | 65 | 4 | 10 | 0.1 | 0 | 204 | 0.52 | 2.21 |

Homogeneous DEA nanogels were synthesized in aqueous solution at 70° C., with added SDS to control the size of the nanogels. It was found that the mixed DEA and DMA solution formed a precipitate above the critical precipitation temperature, either with or without the addition of SDS. Thus, DEA/DMA nanogels with different compositions (from 30 wt % to 60 wt % DMA) were synthesized without SDS at different reaction temperatures (from 37° C. to 64° C.), depending on the DEA/DMA composition. For synthesis of DEA/DMA nanogels with 30 wt % and 40 wt % DMA, the catalyst TEMED was added to decrease the decomposition temperature of the initiator APS.

Example 11

Multi-Angle Laser Light Scattering and Dynamic Light Scattering of the Thermo-Responsive Nanogels A DAWN DSP Laser Photometer-Optilab DSP Interferometric Refractometer system (Wyatt Technology, Santa Barbara, Calif.) was used for static, multi-angle laser light scattering (MALLS) characterization of the weight-average molar mass ($M_w$), the root-mean-square z-average radius of gyration ($R_g$), and the second virial coefficient ($A_2$) of each nanogel preparation in aqueous solution.

In static MALLS, the angular dependence of the excess absolute time-averaged scattered intensity, known as the excess Rayleigh ratio $R_{vv}(q)$, is measured. For a dilute solution with a concentration C (g/mL), $R_{vv}(q)$ measured at a relatively small scattering angle θ can be correlated as (see, e.g., Chu, B. Laser Light Scattering, 2$^{nd}$ ed.; Academic Press: New York, 1991; herein incorporated by reference in its entirety)

$$\frac{KC}{R_{vv}(q)} \cong \frac{1}{M_w}\left(1 + \frac{1}{3}\langle R_g^2\rangle_z q^2\right) + 2A_2 C \quad (1)$$

Here, $K=4\pi n^2 (dn/dC)^2/(N_A \lambda_0^4)$ and the scattering vector $q=(4\pi n/\lambda_0)\sin(dn/dc, n, N_A, $ and $\lambda_0$ being the specific refractive index increment, the solvent refractive index, Avogadro's number, and the wavelength of light in a vacuum, respectively. The values of $M_w$, $R_g$, and $A_2$ were extracted via a Zimm plot, using the Debye-Berry formulism (see, e.g., Buchholz, B.; Barron, A. Electrophoresis 2001, 22, 4118; herein incorporated by reference in its entirety).

The Beckman Coulter N4 Plus (Beckman Coulter, Inc., Fullerton, Calif.) is a commercially available multi-angle dynamic light scattering (DLS) spectrometer relying on a laser with a wavelength of 632.88 nm. The PCS analyzer in the N4 Plus has six fixed measurement angles (11.1°, 15.7°, 23.0°, 30.2°, 62.5°, and 90°). The apparent hydrodynamic diameter of macromolecules or colloids is measured at different angles. Any population of particles that scatter weakly at a certain angle may be masked by particles with strong scattering at that angle. In dynamic LLS, the intensity-intensity time correlation function $G^{(2)}$ (t, q) in the self-beating mode was measured and can be expressed by (see, e.g., Brown, W. Dynamic Light Scattering, Oxford Science Publications, 1993; herein incorporated by reference in its entirety)

$$G^{(2)}(t,q)=\langle I(t,q)I(q,0)\rangle=\langle I(0)\rangle^2 g^{(2)}(t)=\langle I(0)\rangle^2[1+|g^{(1)}(t)|^2] \quad (2)$$

where t is the decay time and $q=(4\pi n/\lambda_0)\sin(\theta/2)$. $g^{(1)}(t)=[\langle E(0)E^*(t)\rangle/\langle E(0E^*(0)\rangle]$ and $g^{(2)}(t)=[\langle I(0)I(t)\rangle/\langle I(0)\rangle^2]$ are the normalized field-field and normalized intensity-intensity autocorrelation functions, respectively.

In practice, the detection area cannot be zero. Therefore, to take into account deviations from ideal correlation, the coherence factor β is introduced into equation (2):

$$g^{(2)}(t)=B(1+\beta|g^{(1)}(q,t)|^2)$$

where B is a measured baseline. The function $g^{(1)}(q,t)$ is related to the line-width distribution G(Γ) by $$g^{(1)}(t, q) = \int_0^\infty G(\Gamma)e^{-\Gamma t}d\Gamma \quad (3)$$

G(Γ) can be obtained from the Laplace inversion of $g^{(1)}(q, t)$, analyzed by a cumulant analysis to get the average line width <Γ> and the relative distribution width $\mu_2/\langle\Gamma\rangle^2$. The extrapolation of Γ/q$^2$ to q→0 allows the estimation of the translational diffusion coefficient (D). Finally, G(Γ) can be converted to the translational diffusion coefficient distribution G(D) and to the hydrodynamic radius distribution $f(R_h)$, using the Stokes-Einstein equation:

$$R_h = \frac{k_B T}{6\pi\eta D} \quad (4)$$

Here, $k_B$, T, and η are the Boltzmann constant, the absolute temperature, and the solvent viscosity, respectively. The dynamic light scattering experiments in this study were performed at a scattering angle of 62.5°.

Figure 7:
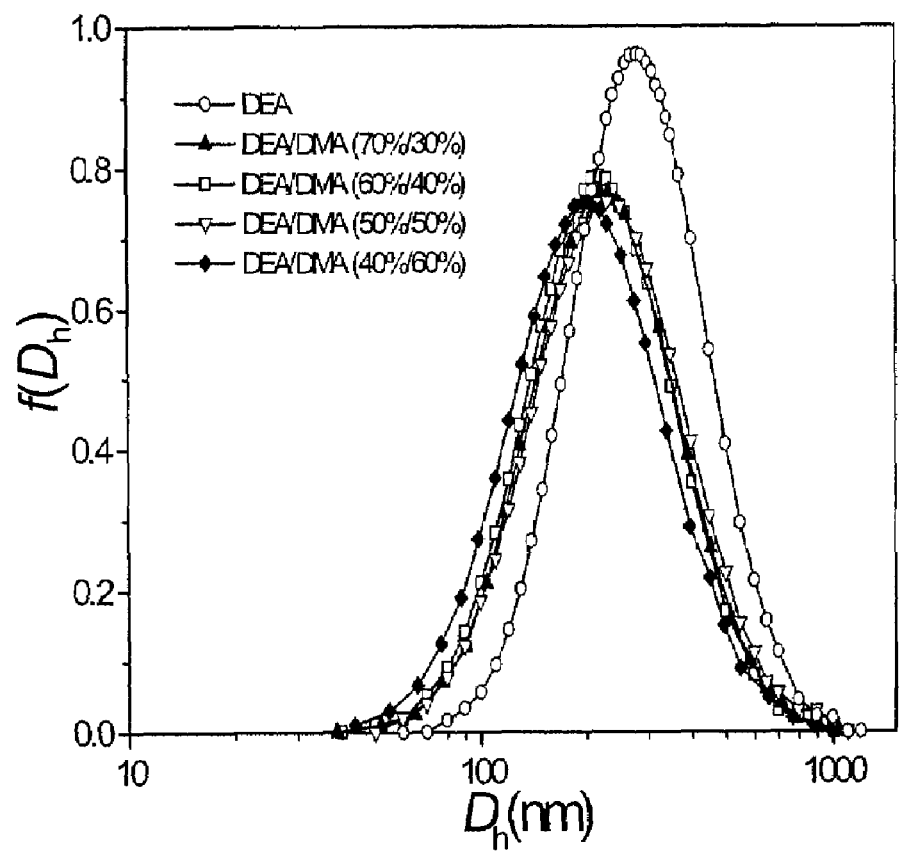
FIG. 7 shows the size distribution of polyDEA nanogels and DEA/DMA nanogels with four different compositions (70%/30%, 60%/40%, 50%/50%, and 40%/60%, w/w) at 20° C.

MALLS studies of the synthesis products showed that the DEA nanogels have by far the highest average molecular weight (1.92×10⁸ g/mole) due to the highly packed polymer chains in the nanogels. The average molecular weights of the DEA/DMA copolymer nanogels ranged from 2.21×10⁷ to 3.89×10⁷ g/mol, dependent on the nanogel size. In the initial syntheses of DEA/DMA nanogels, the concentrations of DEA and DMA monomer, the crosslinker concentration, and the APS initiator concentration were all held constant. The size distributions of nanogels were characterized by DLS, as shown in FIG. 7.

The present invention is not limited to a particular mechanism. Indeed, an understanding of the mechanism is not necessary to practice the present invention. Nonetheless, based upon the DEA nanogels have the narrowest size distribution. The narrow dispersity of DEA nanogels (0.18) was attributed to a strong hydrophobic association at the relative high reaction temperature of 70° C. The polydispersity of the DEA/DMA nanogels ranged from 0.44 to 0.52, and a Gaussian size distribution of the DEA/DMA nanogels was obtained by surfactant-free precipitation polymerization at the appropriate reaction temperature.

Figure 8:
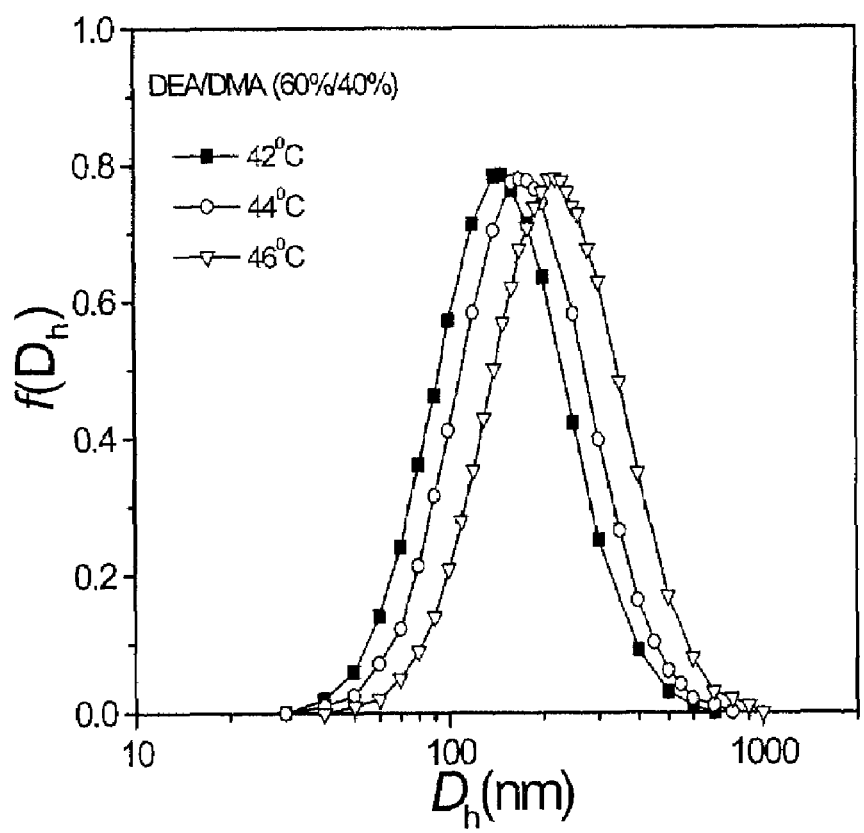
FIG. 8 shows the size distribution of the DEA/DMA (60%/40%, w/w)) nanogels at 20° C., made with the reaction temperatures of 42° C., 44° C., 46° C.

In order to investigate the effects of various synthesis parameters on the size and size distribution of the DEA/DMA nanogels, nanogels that were synthesized over a range of reaction temperatures, reaction times, and crosslinker densities were characterized. It was found that the size of the DEA/DMA nanogels was dependent on the reaction temperature utilized. Copolymer nanogels with a composition of 60% DEA/40% DMA(w/w) were synthesized at 42° C., 44° C., and 46° C. The average hydrodynamic diameter of the nanogels increases with increasing reaction temperature, as shown in FIG. 8, while the different reaction temperatures studied produced nanogels with similar size distributions. The effect of reaction time on the size of polyNIPA microgels has been previously reported (see, e.g., Pelton, R. Adv. Colloid Interface Sci. 2000, 85, 1; Duracher, D.; Elaissari, A.; Pichot, C. Macromol. Symp. 2000, 150, 305; each herein incorporated by reference in their entireties). Pelton found that the size of the microgels remained essentially invariant after one hour of polymerization, even at lower reaction temperatures (see, e.g., Pelton, R. Adv. Colloid Interface Sci. 2000, 85, 1; herein incorporated by reference in its entirety). Experiments conducted during the course of the present invention showed that DEA/DMA (70%/30%) nanogels polymerized for 2 hours or 4 hours exhibit little difference in their size and size distribution.

Figure 9:
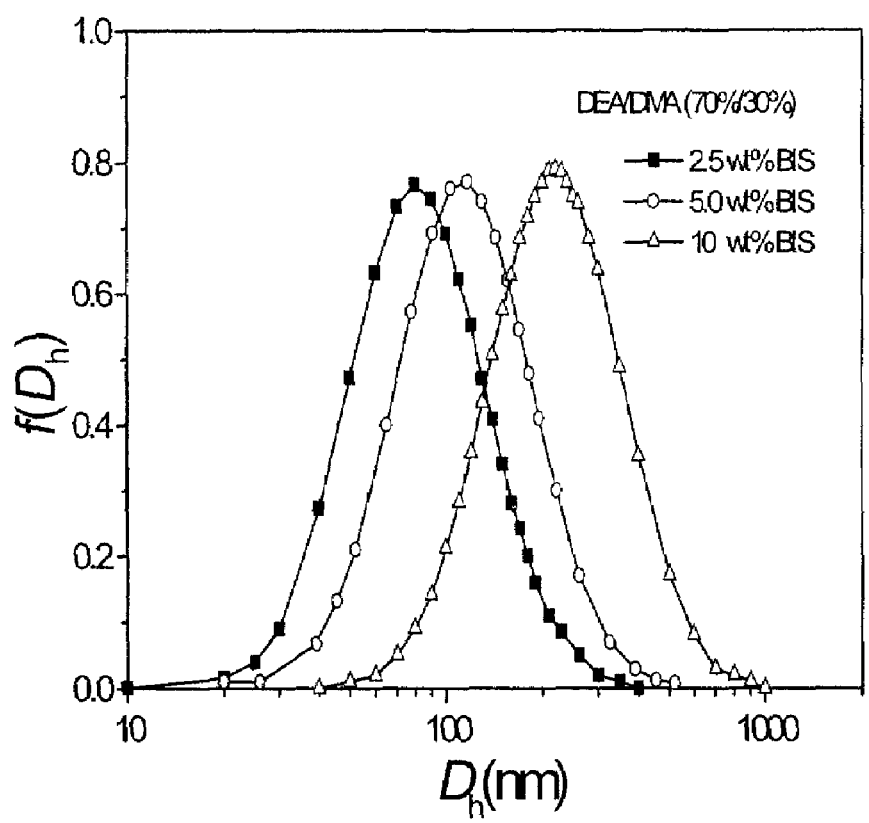
FIG. 9 shows the size distribution of the DEA/DMA (70%/30%, w/w)) nanogels at 20° C. with crosslinker densities of 2.5 wt %, 5.0 wt %, and 10.0% wt of feed monomer DEA, and DMA.

For the preparation of nanogels, the crosslinking density is another important synthesis parameter that usually alters the swelling ratio of the nanogels. Duracher and coworkers studied the influence of crosslinking density on the size of polyNIPA nanogels (see, e.g., Duracher, D., et al., 2000 Macromol. Symp. 150: 305; herein incorporated by reference in its entirety), and reported that an increase in crosslinking density had little effect on the nanogel size below the VPTT, while the size of the collapsed nanogels increased with an increase of the crosslinker density above the VPTT. This implies that crosslinking density only has an influence on the swelling extent of polyNIPA nanogels. DEA/DMA nanogels with crosslinker concentrations of 2.5 wt %, 5.0 wt %, and 10 wt % of the total amount of DEA and DMA monomers were synthesized. The size distributions obtained for the nanogels with different extents of crosslinking are shown in FIG. 9. The results indicated that the size of the DEA/DMA nanogels determined at 20° C. is proportional to the crosslinker concentration, while there is little effect of crosslinking density on the size distribution. The variation of the size with the crosslinker density may be related to the reaction temperature at which the nanogels are made. In the synthesis of DEA/DMA nanogels, the ideal reaction temperature is just a few degrees above the initial phase transition temperature. The present invention is not limited to a particular mechanism. Indeed, an understanding of the mechanism is not necessary to practice the present invention. Nonetheless, the growth of the polymer chains in each nanogel is dependent on the crosslinker concentration, such that higher crosslinker concentration in solution can capture and hold more polymer chains to form larger nanogels.

Example 12

NMR Measurements and Turbidity Measurements of Thermo-Responsive Nanogels $^1$H NMR spectroscopy with a Varian Inova 500 (Walnut Creek, Calif.) was utilized to determine the actual ratio of each monomer incorporated into the DEA/DMA nanogels. In the individual DEA and DMA monomers, there are two $CH_3$ groups. However, in the two monomers these $CH_3$ groups reside in unique chemical environments. The DEA/DMA ratio of the nanogels thus can be measured via the integration of the NMR signals corresponding to the $^1$H of the $CH_3$ groups in DEA and DMA, respectively. The freeze-dried DEA/DMA nanogels (0.04 g) were dissolved in 1 ml of $D_2O$ solvent. $^1$H-NMR (500 MHz, $D_2O$) was then performed, measuring δ (ppm): 1.10 (2 $CH_3$ of DEA, br s), 2.94 (2 $CH_3$ of DMA, br s). DEA/DMA nanogels with four different compositions were studied, as shown in Table 7.

The turbidity of aqueous solutions of thermo-responsive DEA/DMA nanogels was measured by visible light absorbance at 500 nm, using a Cary 500 (Varian, Inc., CA) temperature-controlled spectrophotometer. The Cary 500 is a double-beam UV-VIS-NIR spectrophotometer for high-precision light absorbance experiments in the wavelength range of 175 nm-3300 nm. The temperature-controlled range of this instrument is from −10° C. to 100° C. A Peltier-controlled sample compartment for temperature scan experiments holds a 10×10 mm sample cuvette with a capacity of 2 mL.

Example 13

Characterization of the VPTTs of the Thermo-Responsive Nanogels

Figure 10:
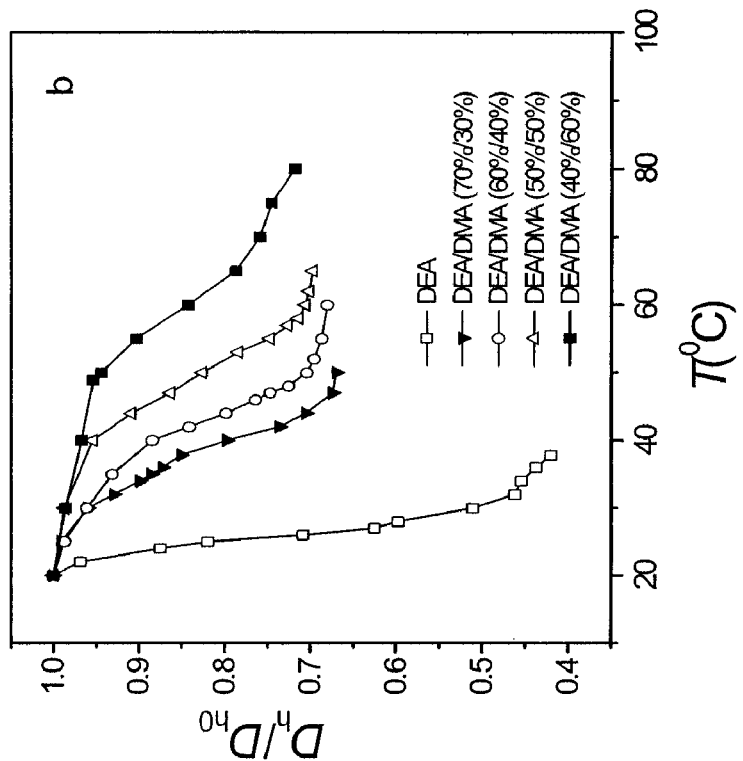
FIG. 10a shows the volume phase transition of DEA/DMA nanogels with four different compositions (70%/30%, 60%/40%, 50%/50%, and 40%/60%, w/w).
FIG. 10b. The de-swelling ratio of polyDEA and DEA/DMA nanogels with four different composition (70%/30%, 60%/40%, 50%/50%, and 40%/60%, w/w).
Figure 10:
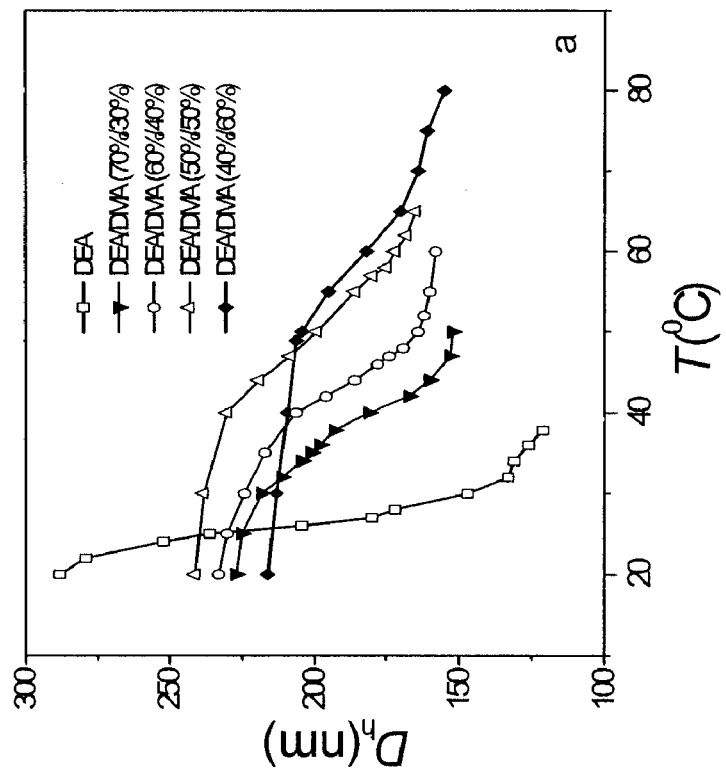

The VPTTs of copolymer nanogels previously reported by others have been varied via the incorporation of ionic comonomers (see, e.g., Zhou, S., Chu, B. J. Phys. Chem. B1998, 102, 1364; Ito, S.; Ogawa, K.; Suzuki, H.; Wang, B.; Yoshida, R.; Kokufuta, E. Langmuir 1999, 15, 4289; each herein incorporated by reference in their entireties). The introduction of ionic groups into nanogels presents two limitations. First, only a small amount of ionic comonomer can be introduced, since larger amounts lead to a loss of the thermosensitivity of the nanogels. For a composition of more than 10 mol % acrylic acid (AA), the VPTT of NIPA/AA nanogels disappears at pH 7.4, because the AA components include ionic groups that strongly absorb water (see, e.g., Ito, S.; Ogawa, K.; Suzuki, H.; Wang, B.; Yoshida, R.; Kokufuta, E. Langmuir 1999, 15, 4289; Chen, G.; Hoffman, A. Nature 1995, 373, 49; each herein incorporated by reference in their entireties). Secondly, it is expected that nanogels with ionic groups are not suitable for some applications of interest, such as electrophoretic DNA separation which requires an electrostatically neutral polymer matrix (see, e.g., Bae, Y. C., Soane, D. J. Chromatogr. 1993, 652, 17; Albarghouthi, M. N., Barron, A. Electrophoresis 2000, 21, 4096; each herein incorporated by reference in their entireties). Non-ionic copolymer nanogels allowing a variation of the VPTT have not been reported. Accordingly, novel thermo-sensitive nanogels were developed consisting solely of the non-ionic monomers DEA and DMA. As shown in FIG. 10a, the phase transition behavior of the DEA/DMA nanogels varies tremendously with the incorporation of different hydrophilic DMA content. Homogeneous polyDEA nanogels undergo a sharp, sigmoidal volume-phase transition with a VPTT at 26° C. An increase in the DMA content results in an increase of the VPTT of the DEA-DMA copolymer nanogels. In contrast to the behavior of the polyDEA nanogels, the DEA/DMA nanogels exhibit broad phase transitions and a relatively low extent of volume collapse with temperature (FIG. 10a). FIG. 10b shows the normalized change in hydrodynamic diameter, $D_h/D_{h0}$, as a function of temperature.

The present invention is not limited to a particular mechanism. Indeed, an understanding of the mechanism is not necessary to practice the present invention. Nonetheless, the corresponding decrease in the size of the DEA/DMA nanogels above the VPTT (FIG. 10a) indicates that the DEA/DMA nanogels are stable and undergo no aggregation in dilute aqueous solution above the VPTT.

It is contemplated that the differing phase transition behavior of the DEA/DMA nanogels should be due, for example, to the hydrophilic/hydrophobic balance of the random copolymer chains. Barker and coworkers (see, e.g., Barker, L.; Cowie, J.; Huckerby, T.; Shaw, D.; Soutar, I.; Swanson, L. Macromolecules 2003, 36, 7765; herein incorporated by reference in its entirety) studied the conformational transition of linear NIPA/DMA copolymers in aqueous solution using TRAMS, fluorescence quenching, and pyrene solubilization. It was found that increasing the DMA content resulted in the adoption of increasingly open conformations above the respective VPTTs of the NIPA/DMA. Thus, NIPA/DMA copolymers exhibit less dramatic collapse transitions and more flexible globules above the VPTT with an increase of the DMA content. Based on these results, it is not surprising, for example, that the DEA/DMA copolymer chains in the nanogels show similar phase transition behavior.

Figure 11:
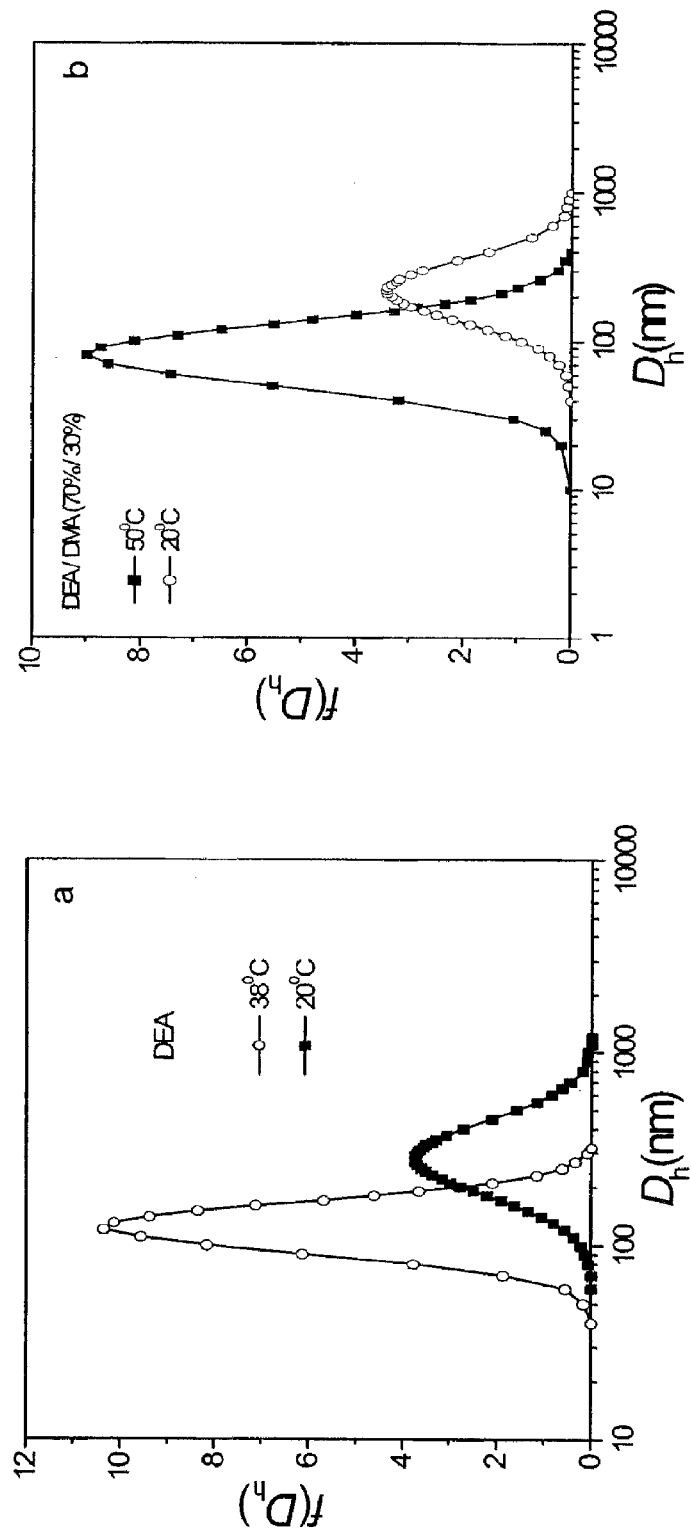
FIG. 11 shows the size distribution of polyDEA nanogels at 20° C. and 38° C. (11a), the size distribution of DEA/DMA nanogels (70%/30%, w/w) at 20° C. and 50° C. (11b), and the size distribution of DEA/DMA nanogels (60%/40%, w/w) at 20° C. and 60° C. (11c).
Figure 11:
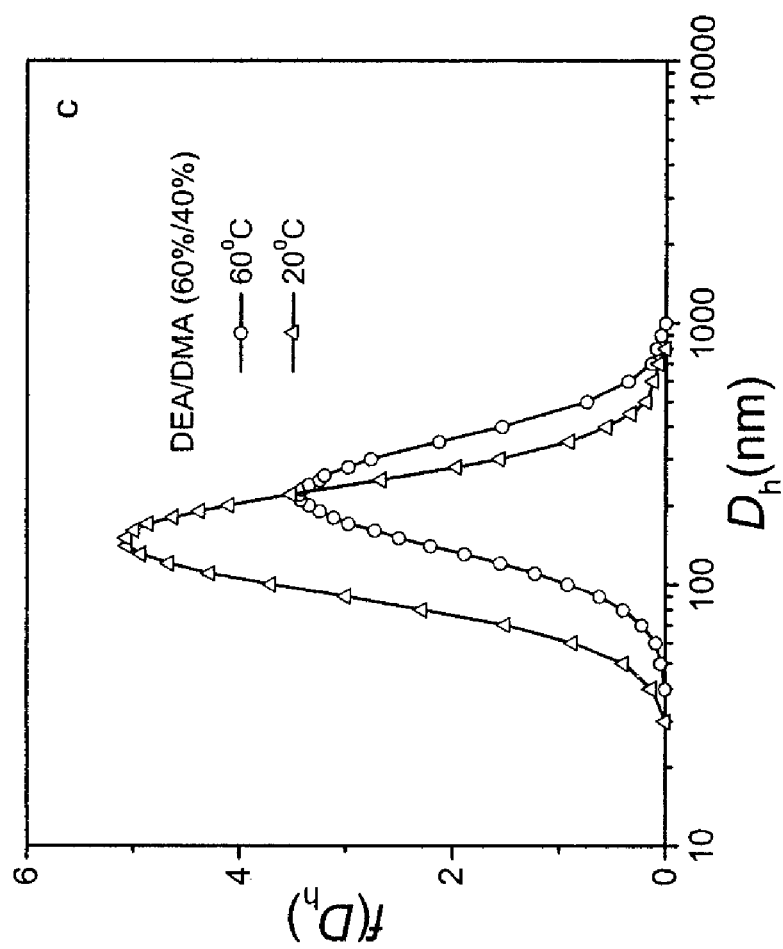

The incorporation of different DMA content also results in a differential change of the size distribution of the DEA/DMA nanogels above respective VPTTs. The homogeneous polyDEA nanogels show a narrower size distribution above the VPTT at 38° C. (FIG. 11a). However, the variation of the size distribution of the DEA/DMA nanogels above the VPTT is dependent on the DMA content. DEA/DMA nanogels with low DMA content (30 wt % DMA) show a narrower distribution above the VPTT (FIG. 11b), while further increase in the DMA content (40 wt % DMA) led to the formation of nanogels that show little change of their size distribution above the VPTT (FIG. 11c).

Figure 12:
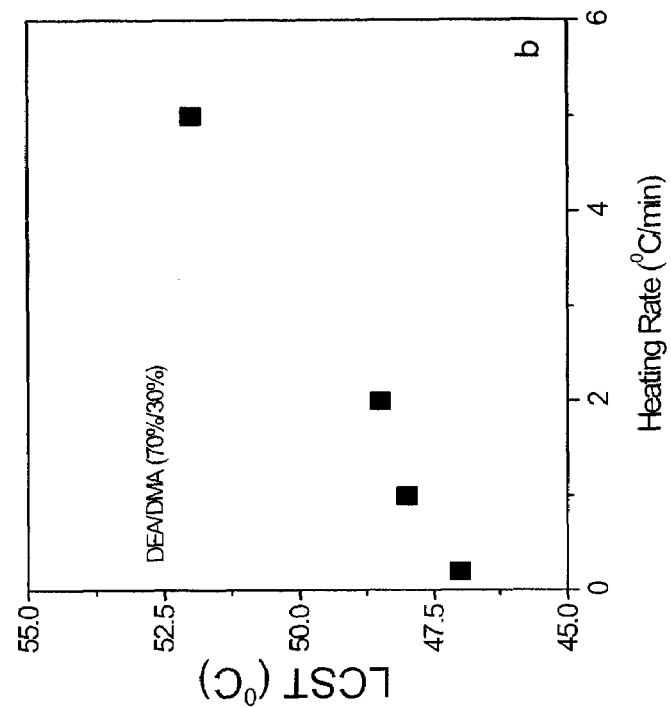
FIG. 12a shows the turbidity changes of DEA/DMA nanogels (70%30%, w/w) with temperature at different heating rates (0.2° C./min, 1° C./min, 2° C./min, and 5° C./min).
FIG. 12b shows effect of heating rate on the LCST of the DEA/DMA (70%/30%, w/w) nanogels.
Figure 12:
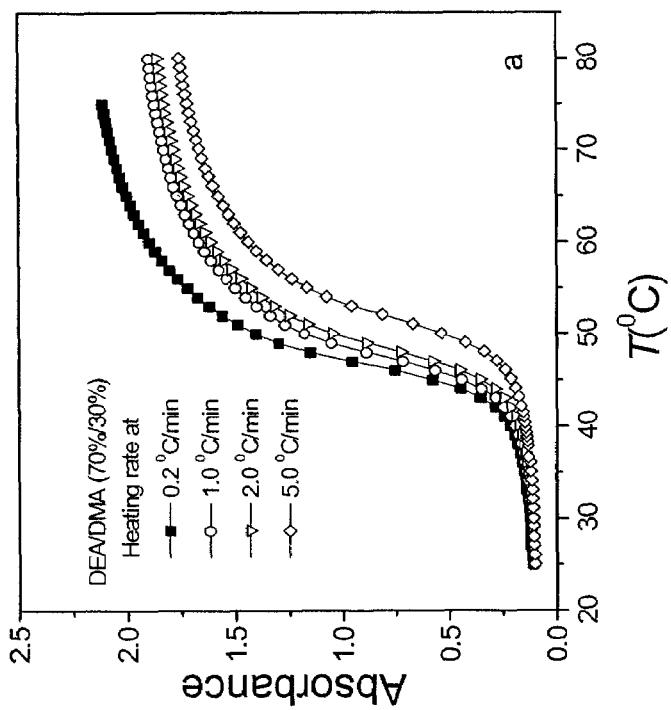

Visible-light absorption spectrophotometry was utilized to study the effects of varying the heating rate, concentration, monomer composition, and salt concentration on the phase transition behavior of the DEA/DMA nanogels. For a 1 wt % DEA/DMA (70%/30%, w/w) nanogel aqueous solution, the heating rates were varied from 5 to 0.2° C./min. As illustrated in FIG. 12a, the heating rate had an influence on the VPTT. Decreasing the heating rate over this range resulted in a shift of the VPTT from 53 to 47° C. Overall, the VPTT of the nanogels (70%/30%, w/w) shows an essentially linear dependence on heating rate in the range studied (FIG. 12b). The present invention is not limited to a particular mechanism. Indeed, an understanding of the mechanism is not necessary to practice the present invention. Nonetheless, it is contemplated that this trend is due to the time-response of the thermally driven VPT of the nanogels. In the linear polymer system, it is established that the volume-phase transition of the polymer in aqueous media occurs via a two-stage mechanism (see, e.g., Fujishige, S.; Kubota, K.; Ando, I. J. Phys. Chem. 1989, 93, 3311; Wu, C.; Zhou, S. Macromolecules 1995, 28, 8381; Winnik, F. M. Polymer 1990, 31, 2125; Chee, C. K.; Rimmer, S.; Soutar, I.; Swanson, L. Polymer 1997, 38, 483; each herein incorporated by reference in their entireties): individual chains collapse from a hydrophilic coil to a hydrophobic globule, prior to aggregation of the hydrophobic globules. In a colloidal nanogel system, a step-wise phase transition of the solution should be attributed to both the polymer-polymer interactions in each nanogel and nanogel-nanogel aggregation. First, the polymer chains in each nanogel are separated from water due to the breaking up of the polymer-water hydrogen bonding above the VPTT. Second, the nanogels shrink, and are colloidally stabilized by electrostatic repulsions at low nanogel concentration. Thus, the phase transition of the nanogels always takes a certain amount of time to reach equilibrium. At a high heating rate, the nanogels experience less sharp, non-equilibrium transition and hence exhibit a higher VPTT.

Figure 13:
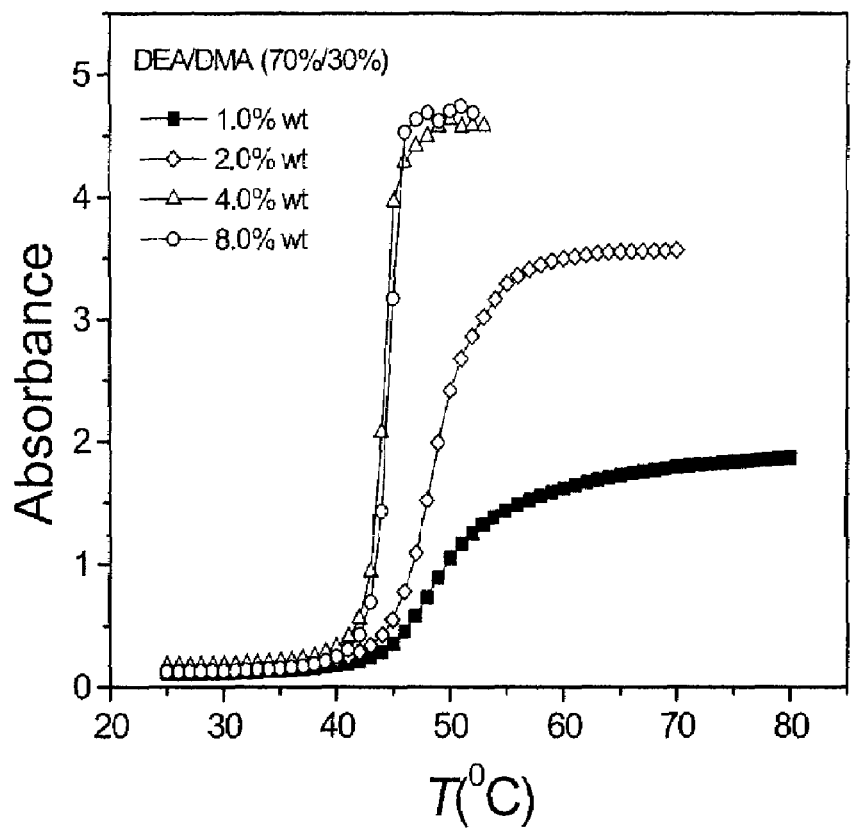
FIG. 13 shows the phase transition behavior of DEA/DMA nanogels (70%/30%, w/w) with temperature at nanogel concentrations of 1.0 wt %, 2.0 wt %, 4.0 wt %, and 8.0 wt %.

In more concentrated dispersions, nanogel-nanogel hydrophobic interactions should be considered in studying the phase transition behavior. FIG. 13 shows the dramatic effect of concentration on the phase transition of DEA-DMA (70%/30%) nanogels. The results show that an increase in concentration from 1 to 4 wt % results in a lower VPTT and a sharper phase transition. At higher concentrations of 4 wt % and 8 wt %, the nanogel solutions exhibited no difference in their phase transition behavior (FIG. 13). The present invention is not limited to a particular mechanism. Indeed, an understanding of the mechanism is not necessary to practice the present invention. Nonetheless, the very sharp phase transition seen for higher concentrations may be due to a very strong aggregation of the nanogels.

Figure 14:
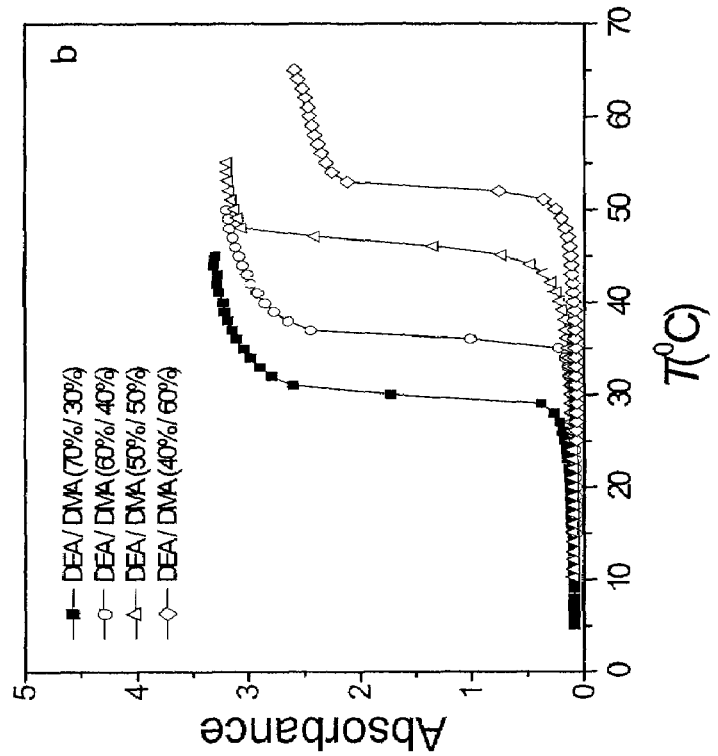
FIG. 14 shows the turbidity changes of the DEA/DMA nanogels with four different compositions (70%/30%, 60%/40%, 50%/50%, and 40%/60%, w/w) in water (14a) and in 1.0M NaCl solution (14b), and the effect of the composition of the DEA/DMA nanogels on the LCST in water and in 1M NaCl (14c).
Figure 14:
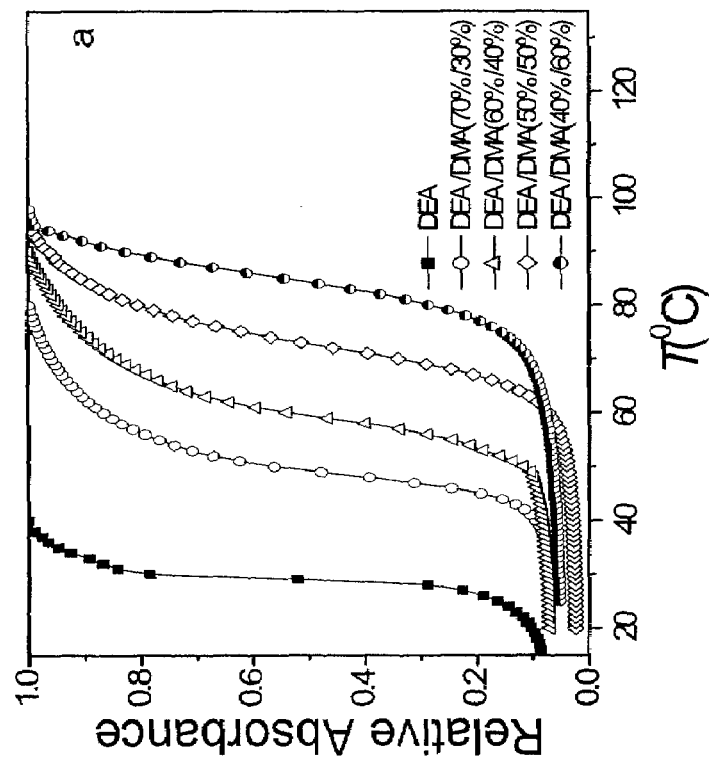
Figure 14:
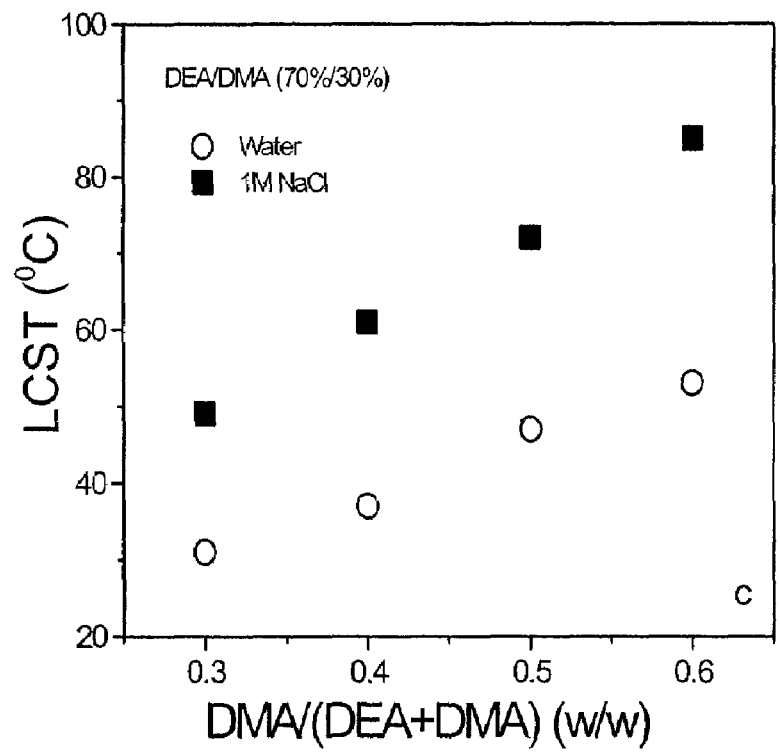

The results discussed above show that the heating rate and concentration strongly influence both the VPTT and the phase transition kinetics of DEA/DMA nanogels. However, the VPTT of the DEA/DMA nanogels is mainly dependent on the composition of the nanogels. In experiments conducted during the course of the present invention, the phase transition behavior of linear DEA/DMA polymers with different compositions was studied by turbidity measurements (see, e.g., Liu, H.; Zhu, X. Polymer 1999, 40, 6985; herein incorporated by reference in its entirety). An increase in the hydrophilic DMA content had a similar effect on the VPTTs of DEA/DMA nanogels, as shown in FIG. 14a. At a 1 wt % concentration, DEA/DMA nanogels of four different compositions exhibit stable nanogel dispersions above their respective phase transition temperature. The present invention is not limited to a particular mechanism. Indeed, an understanding of the mechanism is not necessary to practice the present invention. Nonetheless, the data demonstrate that the phase transition behavior can be tuned with nanogel composition.

Example 14

The Effect of Salt Concentration on the Phase Transition Behavior of Thermo-Responsive Nanogels The electrolyte-induced phase transitions of nonionic polymer gels (see, e.g., Park, T.; Hoffman, A. Macromolecules 1993, 26, 5045; herein incorporated by reference its entirety) and microgels (see, e.g., Daly, E.; Saunders, B.

Langmuir 2000, 16, 5546; Routh, A.; Vincent, B. Langmuir 2002, 18, 5366; each herein incorporated by reference in their entireties) were studied. The electrolytes used were either inorganic salts such as NaCl, KCl, and $CaCl_2$ or organic salts such as $H_4Br$, $(n-C_5H_{11})_4NBr$, and the surfactants SDS and DTAB (dodecyltrimethylammonium bromide) were studied. The addition of inorganic salts resulted in a shift of the VPTT of the polymers to lower temperature (see, e.g., Park, T.; Hoffman, A. Macromolecules 1993, 26, 5045; herein incorporated by reference in its entirety). The effect of organic salts on the VPTT depended on the alkyl chain length (see, e.g., Inomata, H.; Goto, S.; Otake, K.; Saito, S. Langmuir 1992, 8, 687; herein incorporated by reference in its entirety), where some of the salts raised the VPTT and the others lowered the VPTT. Among the inorganic salts, sodium chloride was considered the most effective in controlling the phase transition of the thermo-responsive nanogels. The stability of polyNIPA nanogels in salt-containing aqueous solutions was studied (see, e.g., Daly, E.; Saunders, B. Langmuir 2000, 16, 5546; Routh, A.; Vincent, B. Langmuir 2002, 18, 5366; each herein incorporated by reference in their entireties). The effect of 1M NaCl on the phase transition behavior and the stability of solution of 1 wt % DEA/DMA nanogels with four different compositions was studied. Compared to nanogels in aqueous solution without NaCl (FIG. 14a), the DEA/DMA nanogels exhibited sharper phase transitions in the presence of salt, as shown in FIG. 14b, and lower VPTTs, as shown in FIG. 14c in aqueous solution with 1M NaCl. In contrast to the behavior of stable DEA/DMA nanogels in water, DEA/DMA nanogels were unstable in 1M NaCl aqueous solution above the respective VPTTs, forming a macroscopic precipitate. The present invention is not limited to a particular mechanism. Indeed, an understanding of the mechanism is not necessary to practice the present invention. Nonetheless, based upon this supports a stabilization mechanism based on ionic repulsion between incorporated APS moieties.

Figure 15:
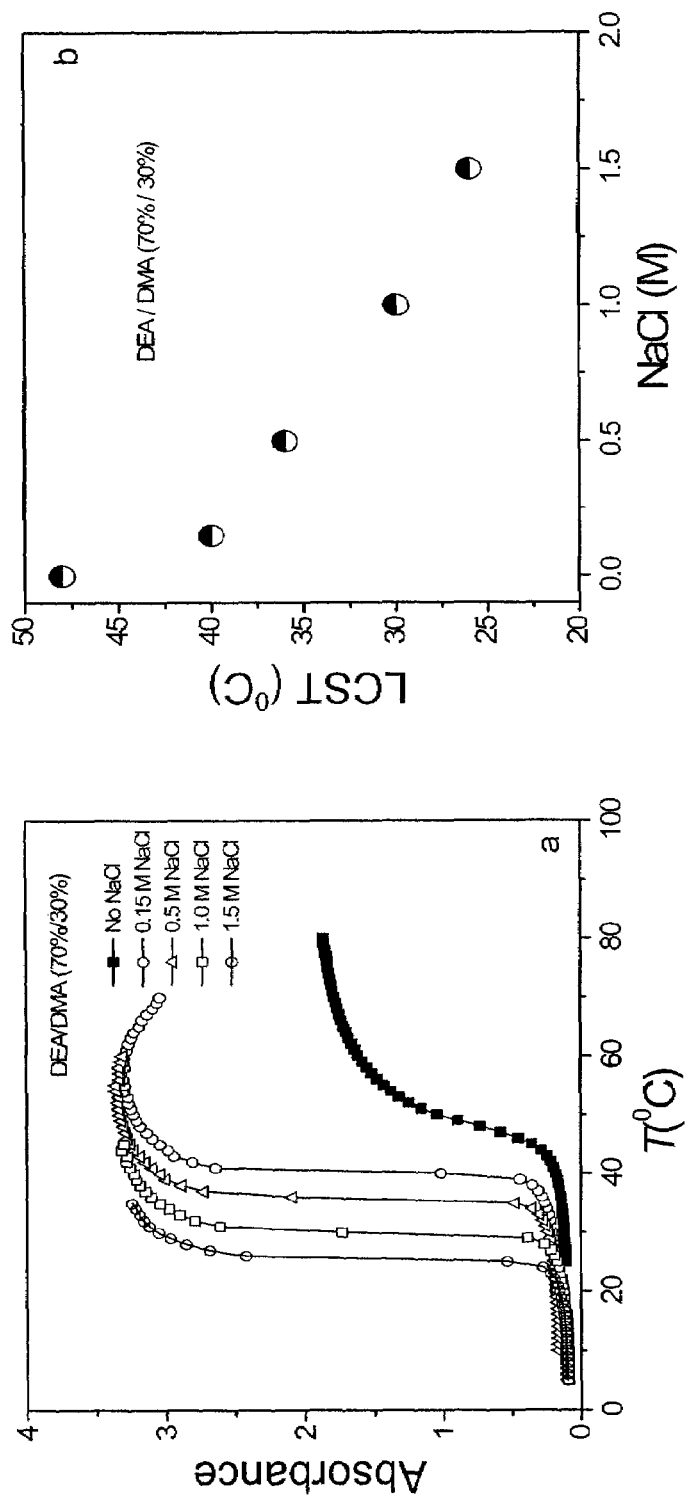
FIG. 15a shows the turbidity changes of the DEA/DMA (70%/30%, w/w) nanogels with temperature at different NaCl concentrations of 0.15 M, 0.5 M, 1.0 M, and 1.5 M.
FIG. 15b shows effect of NaCl concentration on the LCST of the DEA/DMA (70%/30%, w/w) nanogels.
Figure 16:
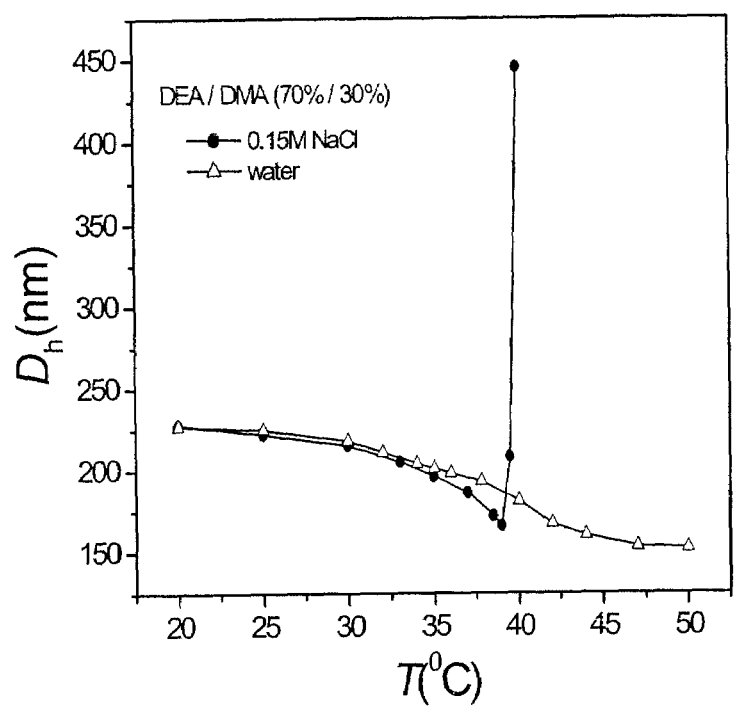
FIG. 16 shows the phase transition behavior of an ultra-dilute DEA/DMA (70%/30%, w/w) nanogel solution (1.2× $10^{-5}$ g/ml) with temperature in the physiological salt concentration of 154 mM NaCl.

The effect of salt concentration on the phase transition behavior of 1 wt % DEA-DMA (70%/30%) nanogels was also studied. FIG. 15 shows that the VPTT of the DEA/DMA nanogels decreased with an increase of NaCl concentration, while the extent of aggregation for the nanogels was much greater than that observed in pure water. In contrast to the stable nanogel dispersions observed in aqueous solution without NaCl, even at 0.15 M NaCl, the DEA/DMA nanogels formed a macroscopic precipitate above the VPTT. The present invention is not limited to a particular mechanism. Indeed, an understanding of the mechanism is not necessary to practice the present invention. Nonetheless, this result shows that NaCl not only decreases the VPTT, but also greatly increased the tendency of nanogels to aggregate. The salt-induced volume-phase transition and aggregation at temperatures above the VPTT may be due to screening of electrostatic repulsion and a disruption of water structure (see, e.g., Inomata, H.; Goto, S.; Otake, K.; Saito, S. Langmuir 1992, 8, 687; herein incorporated by reference in its entirety). In order to monitor the salt effect on the size change and stability of individual nanogels, a very dilute nanogel solution was required. Vincent et al. studied the salt-induced aggregation of the polyNIPA microgels using DLS (see, e.g., Daly, E.; Saunders, B. Langmuir 2000, 16, 5546; herein incorporated by reference in its entirety). It was found that at low salt concentration (<0.2 M), the polyNIPA microgels coagulated at a higher temperature. Moreover, it was found that the polyNIPA microgels coagulated in 1M NaCl at 42° C. but did not phase-separate to form sediment. Stronger coagulation was observed at a low salt concentration, as shown in FIG. 16. The DEA/DMA (70%/30%, w/w) nanogels coagulated at 39° C. at the physiological salt concentration of 0.9% (154 mM). However, the coagulated nanogels did not aggregate to form a macroscopic precipitate. Upon subsequent cooling below the phase transition temperature, the coagulated nanogels re-dispersed in salt solution to form a stable solution.

Aqueous dispersions of DEA and DEA/DMA nanogels exhibited different optical appearances, as shown in FIG. 17. Like polyNIPA nanogel dispersions (see, e.g., Gao, J.; Hu, Z. Langmuir 2002, 18, 1360; herein incorporated by reference in its entirety), DEA nanogel dispersions are opaque at 1 wt % (FIG. 17c) and deep blue at 6 wt % (FIG. 17b) mainly due to light scattering related to nanogel size and inter-nanogel distance. For a low polymer concentration (1 wt %), the nanogel size and inter-nanogel distance are larger than those at a high polymer concentration (6 wt %). The dispersions with large inter-nanogel distance hinder the transmission of visible light, resulting in high turbidity. The present invention is not limited to a particular mechanism. Indeed, an understanding of the mechanism is not necessary to practice the present invention. Nonetheless, for more concentrated DEA nanogel dispersions (6 wt %), the nanogels may deform, entangle, and/or interpenetrate, and hence nanogel size and inter-nanogel distance decrease, leading to blue dispersions. In contrast to DEA nanogels, DEA/DMA nanogel dispersions exhibited a light blue color at 1 wt % (FIG. 17d) and were transparent at 8 wt % (FIG. 17a). Thus, a very small difference of refractive index between nanogels and water resulted in a very low turbidity at low concentration and essentially clear dispersions at high concentration. This is an important observation for the present invention, since optical clarity is important if a polymeric matrix is to be used for DNA separation in conjunction with an optical detection of labeled DNA, for example, with laser-induced fluorescence detection of fluorescently labeled DNA molecules. Here, the present invention shows solutions at an appropriately selected concentration in aqueous media form optically clear solutions which could be used as DNA electrophoresis media.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. A polymeric nanogel composition comprising a sparsely cross-linked polymer structure, wherein said polymeric nanogel is formed from the polymerization of a water-soluble monomer used in the formation of polymers used for electrophoretic separation of nucleic acids, wherein said polymer comprises a water-soluble monomer cross-linked by from about $1\times10^{-8}$ mol % to about $1\times10^{-3}$ mol % non-ionic, hydrophilic cross-linking moiety as compared to the amount of water-soluble monomer present.

2. The composition of claim 1, wherein said water-soluble monomer is selected from the group consisting of acrylamide, N,N-dimethylacrylamide (DMA), N,N-diethylacrylamide (DEA), ethylene oxide, N-hydroxy ethylacyrlamide, N-ethyoxyethylacrylamide, and N-methoxyethylacrylamide.

3. The composition of claim 1, wherein said non-ionic, hydrophilic cross-linking moiety is selected from the group consisting of 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethylene glycol diacrylate, ethylene glycol methacrylate, 1,6-hexanediol diacrylate, 1,6-hexanediol dimethacrylate, neopentyl glycol dimethacrylate, polyethylene glycol diacrylate, polyethylene glycol dimethylacrylate, tryethylene glycol diacrylate, tryethylene glycoldimethylacrylate, tripropylene glycol diacrylate, tetraethylene glycol diacrylate, tetraethylene glycol dimethylacrylate, divinyl esters of a polycarboxylic acid, diallyl esters of a polycarboxylic acid, diallyl maleate, diallyl fumarate, hexamthylenebismaleimide, divinyl adipate, diallyl succinate, a divinyl ether of ethylene glycol, cylcopentadiene diacrylate, N,N'-methylenebisacrylamide, N,N'-methylenebismethacrylamide, ethylene glycol dimethylacrylate and mixtures thereof.

4. The composition of claim 1, wherein said hydrophilic cross-linking moiety is present in an amount selected from the group consisting of $1\times10^{-8}$ mol % as compared to amount of water-soluble monomer present, about $1\times10^{-7}$ mol % as compared to amount of water-soluble monomer present, about $1\times10^{-6}$ mol % as compared to amount of water-soluble monomer present, about $1\times10^{-5}$ mol % as compared to amount of water-soluble monomer present, about $1\times10^{-4}$ mol % as compared to amount of water-soluble monomer present, and about $1\times10^{-3}$ mol % as compared to amount of water-soluble monomer present.

5. The composition of claim 1, wherein said nanogel composition has a matrix having low shear viscosity from about 300 centipoise to about 200,000 centipoise when said polymeric nanogel material is dissolved in an aqueous buffer.

6. The composition of claim 1, wherein said polymer is formed using inverse emulsion polymerization.

7. A nanogel composition comprising a sparsely cross-linked polymeric material used for electrophoretic separation of nucleic acids formed from the polymerization of a water-soluble monomer mixture, wherein said water-soluble monomer mixture comprises at least two monomer agents, wherein the volume phase transition temperature of said nanogel composition is dependent upon the percent by weight of each of said at least two monomer agents in said water-soluble monomer mixture.

8. The nanogel composition of claim 7, wherein said at least two monomer agents are selected from the group consisting of acrylamide, DMA, DEA, ethylene oxide, N-hydroxy ethylacyrlamide, N-ethyoxyethylacrylamide, and N-methoxyethylacrylamide.

9. The nanogel composition of claim 7, wherein said at least two monomer agents are DEA and DMA.

10. The nanogel composition of claim 9, wherein said monomer mixture is 40% wt DEA and 60% wt DMA.

11. The nanogel composition of claim 9, wherein said monomer mixture is 50% wt DEA and 50% wt DMA.

12. The nanogel composition of claim 9, wherein said monomer mixture is 60% wt DEA and 40% wt DMA.

13. The nanogel composition of claim 9, wherein said monomer mixture is 70% wt DEA and 30% wt DMA.

14. The nanogel composition of claim 9, wherein said monomer mixture is about 30% wt DEA and 70% wt DMA.

* * * * *